(12) United States Patent
Osborne et al.

(10) Patent No.: US 6,991,002 B2
(45) Date of Patent: Jan. 31, 2006

(54) TAMPER EVIDENT SYRINGE TIP CAP AND AUTOMATED METHOD FOR PREPARING TAMPER-EVIDENT SYRINGES

(75) Inventors: Joel A. Osborne, Port Orange, FL (US); Jose R. Gonzalez, Ormond Beach, FL (US); Dennis Tribble, Ormond Beach, FL (US)

(73) Assignee: ForHealth Technologies, Inc., Daytona Beach, FL (US)

( * ) Notice: Subject to any disclaimer, the term of this patent is extended or adjusted under 35 U.S.C. 154(b) by 123 days.

(21) Appl. No.: 10/728,363

(22) Filed: Dec. 3, 2003

(65) Prior Publication Data

US 2005/0004706 A1 Jan. 6, 2005

Related U.S. Application Data

(60) Provisional application No. 60/430,481, filed on Dec. 3, 2002, and provisional application No. 60/470,328, filed on May 13, 2003.

(51) Int. Cl.
  *B65B 1/04* (2006.01)

(52) U.S. Cl. .................. 141/27; 141/21; 604/416; 53/282; 53/426

(58) Field of Classification Search .............. 141/1, 141/2, 18, 21–29; 604/416; 53/281–282, 53/381.4, 468, 471, 492, 284.5, 381.2, 284.6, 53/425, 426, 167
See application file for complete search history.

(56) References Cited

U.S. PATENT DOCUMENTS

| | | |
|---|---|---|
| 2,880,723 A | 4/1959 | Adams |
| 2,981,432 A | 4/1961 | Flood |
| 3,200,486 A | 8/1965 | Shields |
| 3,527,017 A | 9/1970 | Taylor et al. |
| 3,736,933 A | 6/1973 | Szabo |
| 3,823,818 A | 7/1974 | Shaw |
| 3,835,897 A | 9/1974 | Gess |
| 3,848,485 A | 11/1974 | Grenci |
| 3,865,236 A | 2/1975 | Rycroft |
| 3,880,211 A | 4/1975 | Gess |
| 4,472,357 A | 9/1984 | Levy et al. |
| 4,502,616 A | 3/1985 | Meierhoefer |
| 4,512,475 A | 4/1985 | Federighi |
| 4,624,148 A | 11/1986 | Averette |
| 4,639,250 A | 1/1987 | Rycroft |
| 4,674,652 A | 6/1987 | Aten et al. |
| 4,758,230 A | 7/1988 | Rycroft |
| 4,773,285 A | 9/1988 | Dionne |
| 4,861,335 A | 8/1989 | Reynolds |

(Continued)

Primary Examiner—Steven O. Douglas
(74) Attorney, Agent, or Firm—Darby & Darby

(57) ABSTRACT

In one exemplary embodiment, an automated medication preparation system including a plurality of automated syringe preparation stations is provided and includes (1) a first automated gripper for removing a tip cap from a barrel of one syringe and placing the removed tip cap at a first location; (2) an automated device having a positionable cannula that is operatively connected to an aspirating device for drawing a prescribed dosage amount of medication from a supply and delivering the dosage to the syringe by injecting the medication through the cannula and into uncapped barrel in a just-in-time for use manner; (3) a second automated gripper for replacing the removed tip cap on the syringe barrel after the medication is injected therein; and (4) a station for making the syringe tamper evident that includes an instrument for joining the tip cap to the syringe luer connector in a localized area (e.g., tamper evident spot weld and sealed bags) so as to restrict the twisting and removal of the tip cap, thereby providing a tamper evident syringe.

38 Claims, 31 Drawing Sheets

U.S. PATENT DOCUMENTS

| | | |
|---|---|---|
| 4,865,592 A | 9/1989 | Rycroft |
| 4,944,736 A | 7/1990 | Holtz |
| 5,040,437 A | 8/1991 | Mueller |
| 5,256,154 A | 10/1993 | Liebert et al. |
| 5,341,854 A | 8/1994 | Zezulka et al. |
| 5,356,393 A | 10/1994 | Haber et al. |
| 5,496,288 A | 3/1996 | Sweeney |
| 5,542,935 A | 8/1996 | Unger et al. |
| 5,597,530 A | 1/1997 | Smith et al. |
| 5,651,775 A | 7/1997 | Walker et al. |
| 5,704,921 A | 1/1998 | Carilli |
| 5,735,181 A | 4/1998 | Anderson |
| 5,805,454 A | 9/1998 | Valerino, Sr. et al. |
| 5,826,409 A | 10/1998 | Slepicka et al. |
| 5,855,839 A | 1/1999 | Brunel |
| 5,884,457 A * | 3/1999 | Ortiz et al. .................... 53/468 |
| 5,899,889 A | 5/1999 | Futagawa et al. |
| 5,911,252 A | 6/1999 | Cassel |
| 6,027,472 A | 2/2000 | Kriesel et al. |
| 6,048,086 A | 4/2000 | Valerino, Sr. |
| 6,068,614 A | 5/2000 | Kimber et al. |
| 6,142,039 A | 11/2000 | Herring, Sr. |
| 6,877,530 B2 * | 4/2005 | Osborne et al. ............... 141/27 |
| 2002/0020459 A1 | 2/2002 | Baldwin et al. |

\* cited by examiner

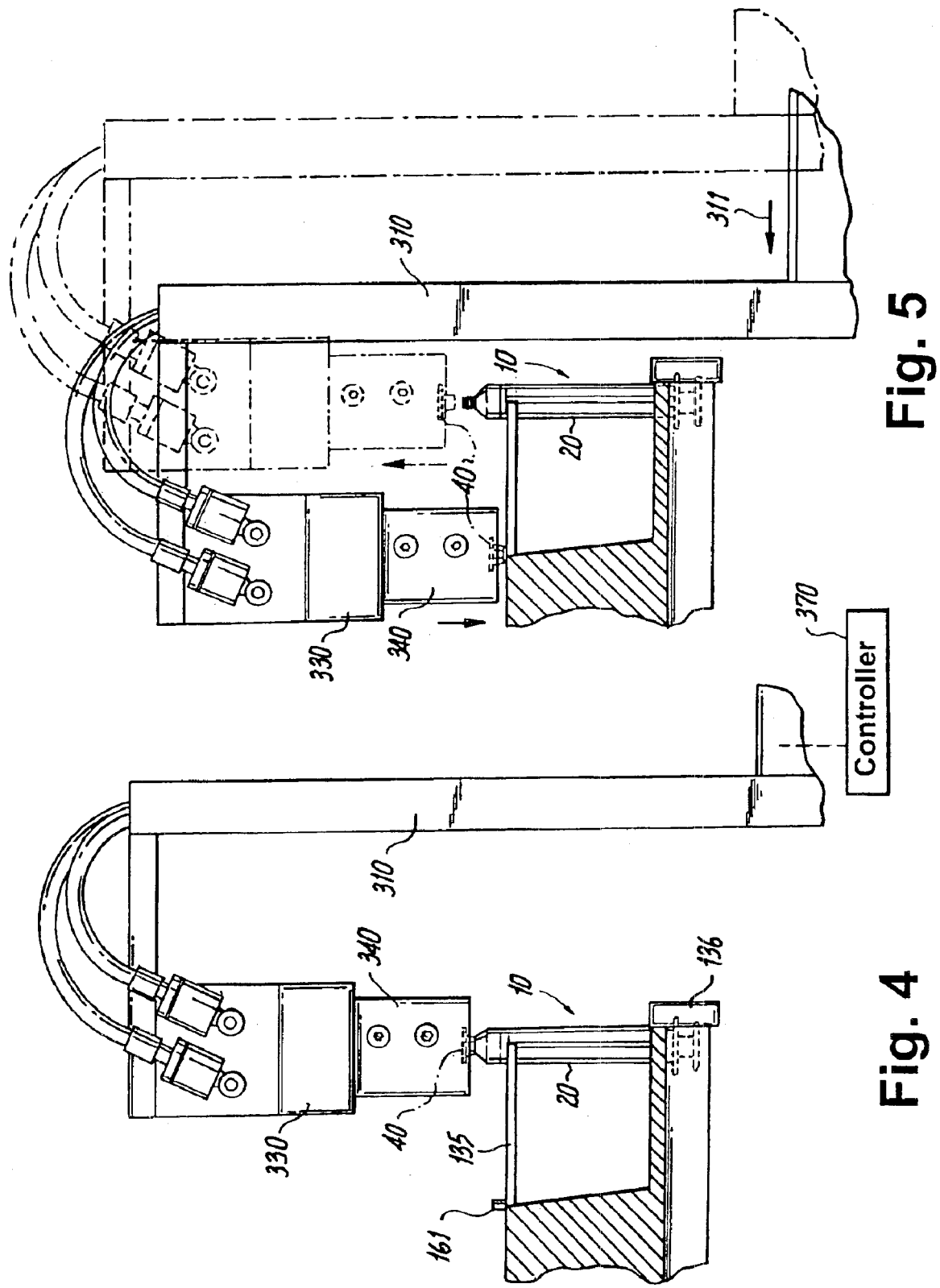

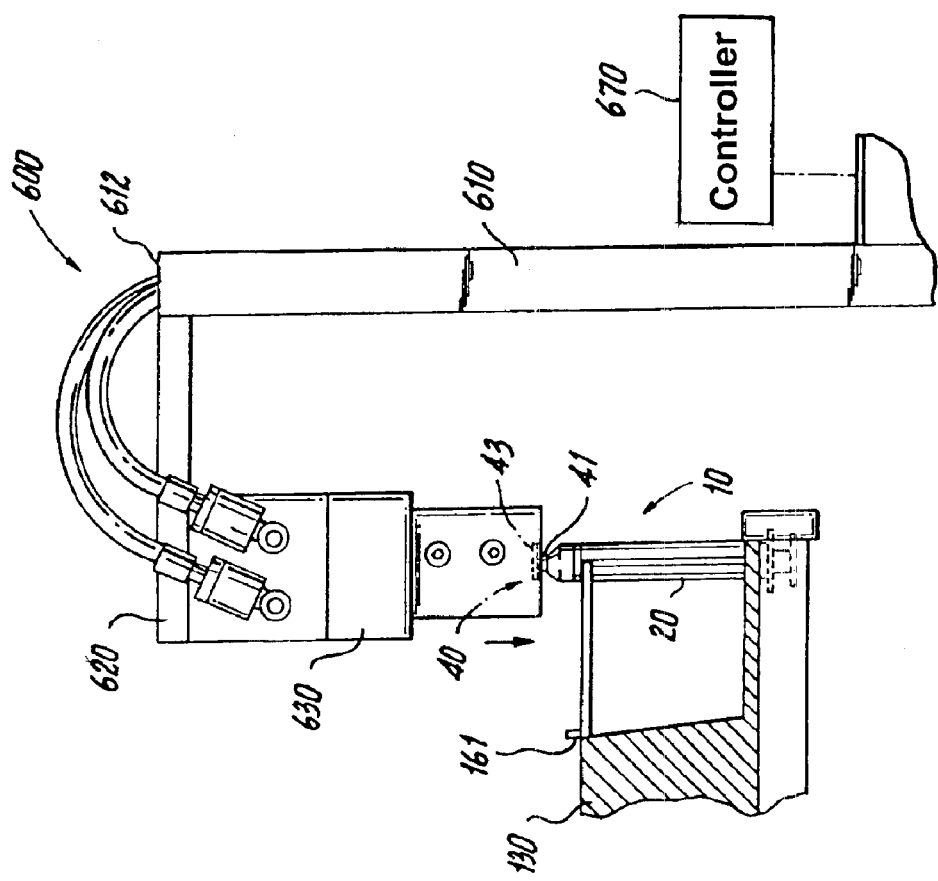
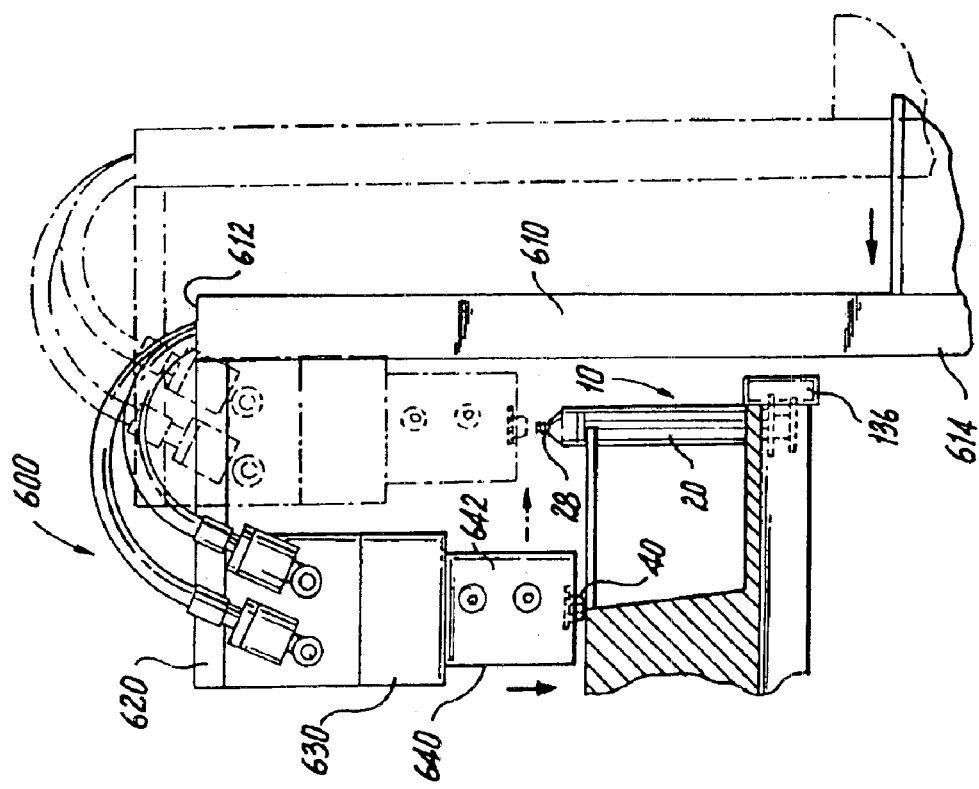
Fig. 26
Fig. 25

TAMPER EVIDENT SYRINGE TIP CAP AND AUTOMATED METHOD FOR PREPARING TAMPER-EVIDENT SYRINGES

CROSS-REFERENCE TO RELATED APPLICATION

This application claims the benefit of U.S. patent application Ser. No. 60/430,481, filed Dec. 3, 2002, and U.S. patent application Ser. No. 60/470,328, filed May 13, 2003, each of which is hereby incorporated by reference in its entirety.

TECHNICAL FIELD

The present invention relates generally to medical and pharmaceutical equipment, and more particularly, to an automated apparatus for preparing a syringe to receive a unit dose of medication; dispensing the unit dose of medication to the syringe; and then preparing the syringe for use including the formation of a tamper evident feature associated with the tip cap of a filled syringe to indicate whether the syringe has been tampered with after the filling thereof.

BACKGROUND

Disposable syringes are in widespread use for a number of different types of applications. For example, syringes are used not only to withdraw a fluid (e.g., blood) from a patient but also to administer a medication to a patient. In the latter, a cap or the like is removed from the syringe and a unit dose of the medication is carefully measured and then injected or otherwise disposed within the syringe.

As technology advances, more and more sophisticated, automated systems are being developed for preparing and delivering medications by integrating a number of different stations, with one or more specific tasks being performed at each station. For example, one type of exemplary automated system operates as a syringe filling apparatus that receives user inputted information, such as the type of medication, the volume of the medication and any mixing instructions, etc. The system then uses this inputted information to disperse the correct medication into the syringe up to the inputted volume.

In some instances, the medication that is to be delivered to the patient includes more than one pharmaceutical substance. For example, the medication can be a mixture of several components, such as several pharmaceutical substances.

By automating the medication preparation process, increased production and efficiency are achieved. This results in reduced production costs and also permits the system to operate over any time period of a given day with only limited operator intervention for manual inspection to ensure proper operation is being achieved. Such a system finds particular utility in settings, such as large hospitals, including a large number of doses of medications that must be prepared daily. Traditionally, these doses have been prepared manually in what is an exacting but tedious responsibility for a highly skilled staff. In order to be valuable, automated systems must maintain the exacting standards set by medical regulatory organizations, while at the same time simplifying the overall process and reducing the time necessary for preparing the medications.

Because syringes are used often as the carrier means for transporting and delivering the medication to the patient, it is advantageous for these automated systems to be tailored to accept syringes. However, the previous methods of dispersing the medication from the vial and into the syringe were very time consuming and labor intensive. More specifically, medications and the like are typically stored in a vial that is sealed with a safety cap or the like. In conventional medication preparation, a trained person retrieves the correct vial from a storage cabinet or the like, confirms the contents and then removes the safety cap manually. This is typically done by simply popping the safety cap off with one's hands. Once the safety cap is removed, the trained person inspects the integrity of the membrane and cleans the membrane. An instrument, e.g., a needle, is then used to pierce the membrane and withdraw the medication contained in the vial. The withdrawn medication is then placed into a syringe to permit subsequent administration of the medication from the syringe.

FIG. 1 illustrates an exemplary conventional syringe 10 that includes a barrel 20 having an elongated body 22 that defines a chamber 30 that receives and holds a medication that is disposed at a later time. The barrel 20 has an open proximal end 24 with a flange 25 being formed thereat and it also includes an opposing distal end 26 that has a barrel tip 28 that has a passageway 29 formed therethrough. One end of the passageway 29 opens into the chamber 30 to provide communication between the barrel tip 28 and the chamber 30 and the opposing end of the passageway 29 is open to permit the medication to be dispensed through a cannula (not shown) or the like that is later coupled to the barrel tip 28.

An outer surface of the barrel tip or luer 28 can include features to permit fastening with a cap or other type of enclosing member. For example, the luer can have threads 27 that permit a tip cap 40 to be securely and removably coupled to the barrel tip 28. The tip cap 40 thus has complementary fastening features that permit it to be securely coupled to the barrel tip or luer 28. The tip cap 40 is constructed so that it closes off the passageway 29 to permit the syringe 10 to be stored and/or transported with a predetermined amount of medication disposed within the chamber 30. As previously mentioned, the term "medication" refers to a medicinal preparation for administration to a patient and most often, the medication is contained within the chamber 30 in a liquid state even though the medication initially may have been in a solid state, which was processed into a liquid state.

The syringe 10 further includes a plunger 50 that is removably and adjustably disposed within the barrel 20. More specifically, the plunger 50 is also an elongated member that has a proximal end 52 that terminates in a flange 54 to permit a user to easily grip and manipulate the plunger 50 within the barrel 20. Preferably, the plunger flange 54 is slightly smaller than the barrel flange 25 so that the user can place several fingers around, against, or near the barrel flange 25 to hold the barrel 20 and then use fingers of the other hand to withdraw or push the plunger 50 forward within the barrel 20. An opposite distal end 56 of the plunger 50 terminates in a stopper 59 or the like that seals against the inner surface of the barrel 20 within the chamber 30. The plunger 50 can draw a fluid (e.g., air or a liquid) into the chamber 30 by withdrawing the plunger 50 from an initial position where the stopper 59 is near or at the barrel tip or luer 28 to a position where the stopper 59 is near the proximal end 24 of the barrel 20. Conversely, the plunger 50 can be used to expel or dispense medication by first withdrawing the plunger 50 to a predetermined location, filling the chamber 30 with medication and then applying force against the flange 54 so as to move the plunger 50 forward within the chamber 30, resulting in a decrease in the volume of the chamber 30 and therefore causing the medication to be forced into and out of the barrel tip or luer 28.

As is known, the safety of the patient is of utmost importance and therefore, the various medication processing and manufacturing equipment typically incorporate various safety features that indicate to a user (patient) whether the product may have been tampered with at an earlier time. For example, a container that houses solid medication, such as pills, tablets, or capsules, often includes a tamper proof label that extends and is sealed across the top opening of the container underneath the cap. Thus, when a consumer initially purchases the product and unscrews the cap, the tamper proof label should be fully intact and sealed across the opening of the container. If the label is not intact, the consumer should not use the medication contained therein and instead should report the incident and discard the bottle and its contents. Other types of tamper evident sealing are also know for indicating to the consumer or patient whether the product may have been tampered with and therefore, should not be used for the sake of safety.

What is needed in the art and has heretofore not been available is a system and method for automating the medication preparation process and more specifically, an automated system and method for preparing a syringe including the filling of medication therein and also an automated station for providing a tamper evident feature to the syringe.

SUMMARY

In one exemplary embodiment, an automated medication preparation system including a plurality of automated syringe preparation stations is provided and includes (1) a first automated gripper for removing a tip cap from a barrel of one syringe and placing the removed tip cap at a first location; (2) an automated device having a positionable cannula that is operatively connected to an aspirating device for drawing a prescribed dosage amount of medication from a supply and delivering the dosage to the syringe by injecting the medication through the cannula and into uncapped barrel in a just-in-time for use manner; (3) a second automated gripper for replacing the removed tip cap on the syringe barrel after the medication is injected therein; and (4) a tamper evident processing station that includes an instrument for joining the tip cap to the syringe barrel in a localized area (e.g., spot weld or tamper evident tape) so as to restrict the twisting and removal of the tip cap, thereby providing evidence that the contents of the syringe are intact as filled (tamper evidence).

In one exemplary embodiment, the tamper evident processing station is a heat-staking station and the instrument is in the form of a heated wire, rod, or probe that is placed into contact with or in close proximity to the tip cap to cause the tip cap to join the syringe barrel in the local area. In other words, a local spot weld is formed between the tip cap and the syringe barrel. In one embodiment and depending upon the shape of the instrument, the bond is in the form of a substantially circular spot weld. As the user removes the tip cap from the syringe prior to use, the user will feel noticeable resistance to cap movement and will hear a pronounced "snap" when the tip cap is twisted from the syringe. This resistance and "snap" signals that the syringe contents are intact and have not been tampered with nor has the tip cap has been inadvertently removed and replaced after the syringe was prepared.

Moreover, a laser can be used at the tamper evident processing station to emit a laser beam which is directed to the tip cap to cause the melting and bonding of the tip cap to the syringe barrel in a local area, thereby forming a spot weld.

In yet another embodiment, the tamper evident processing station includes an ultrasonic welder and the instrument is used to join the tip cap to the syringe barrel through pressure and high frequency mechanical vibrations, creating localized frictional heat that melts the tip cap and the syringe barrel, both of which are formed of a plastic material. When the vibrations stop, the plastic quickly cools and solidifies, thereby forming the spot weld.

Further aspects and features of the exemplary automated safety cap removal mechanism disclosed herein can be appreciated from the appended Figures and accompanying written description.

BRIEF DESCRIPTION OF THE DRAWINGS

FIG. 4 is a sectional elevation view of the automated device of FIG. 3 engaging the safety syringe tip cap;

FIG. 5 is a sectional elevation view of the automated device of FIG. 3 showing removal and placement of the safety tip cap on a post of a rotary device;

FIG. 25 is a sectional elevation view of an automated device for placing the safety tip cap back on the syringe with the device being shown engaging the safety syringe tip cap disposed on the rotary device and removing it therefrom;

FIG. 26 is a sectional elevation view of the automated device of FIG. 25 showing placement of the safety tip cap back on the syringe.

DETAILED DESCRIPTION OF PREFERRED EMBODIMENTS

Figure 1:
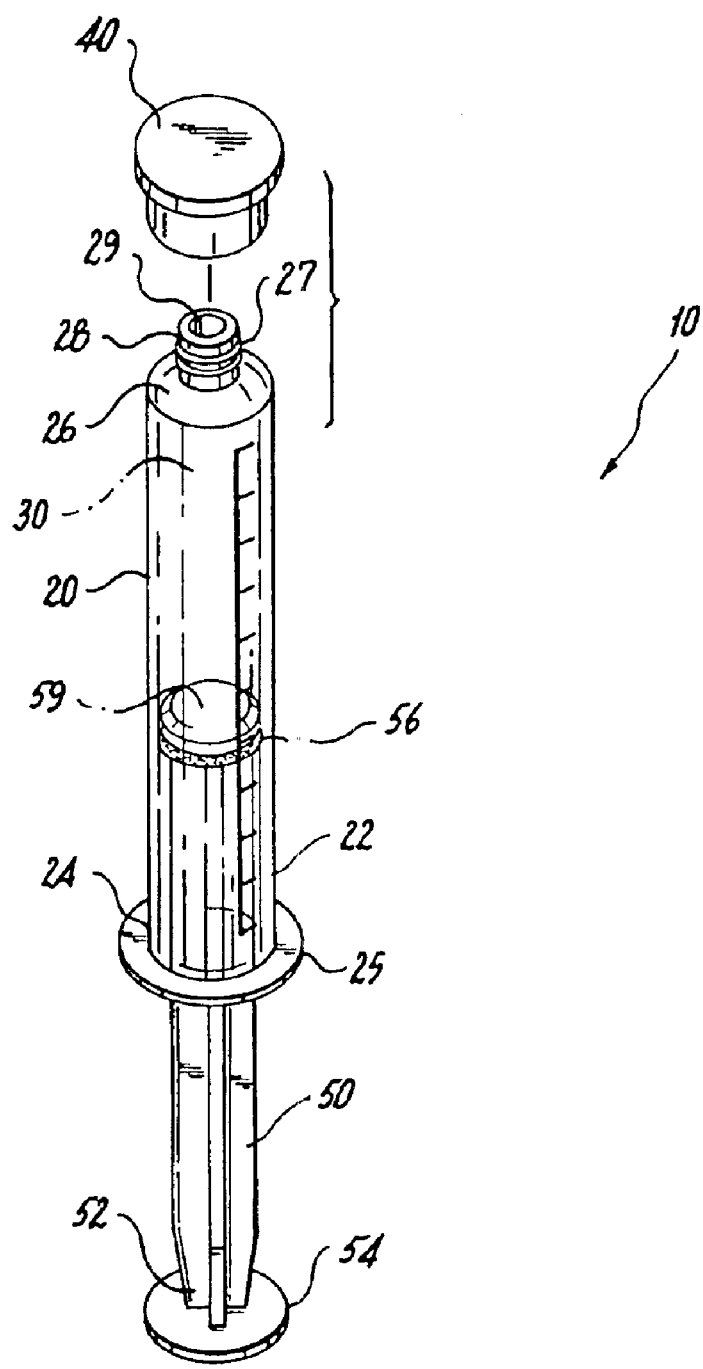
FIG. 1 is a perspective view of a conventional syringe having a safety tip cap removed therefrom.
Figure 2:
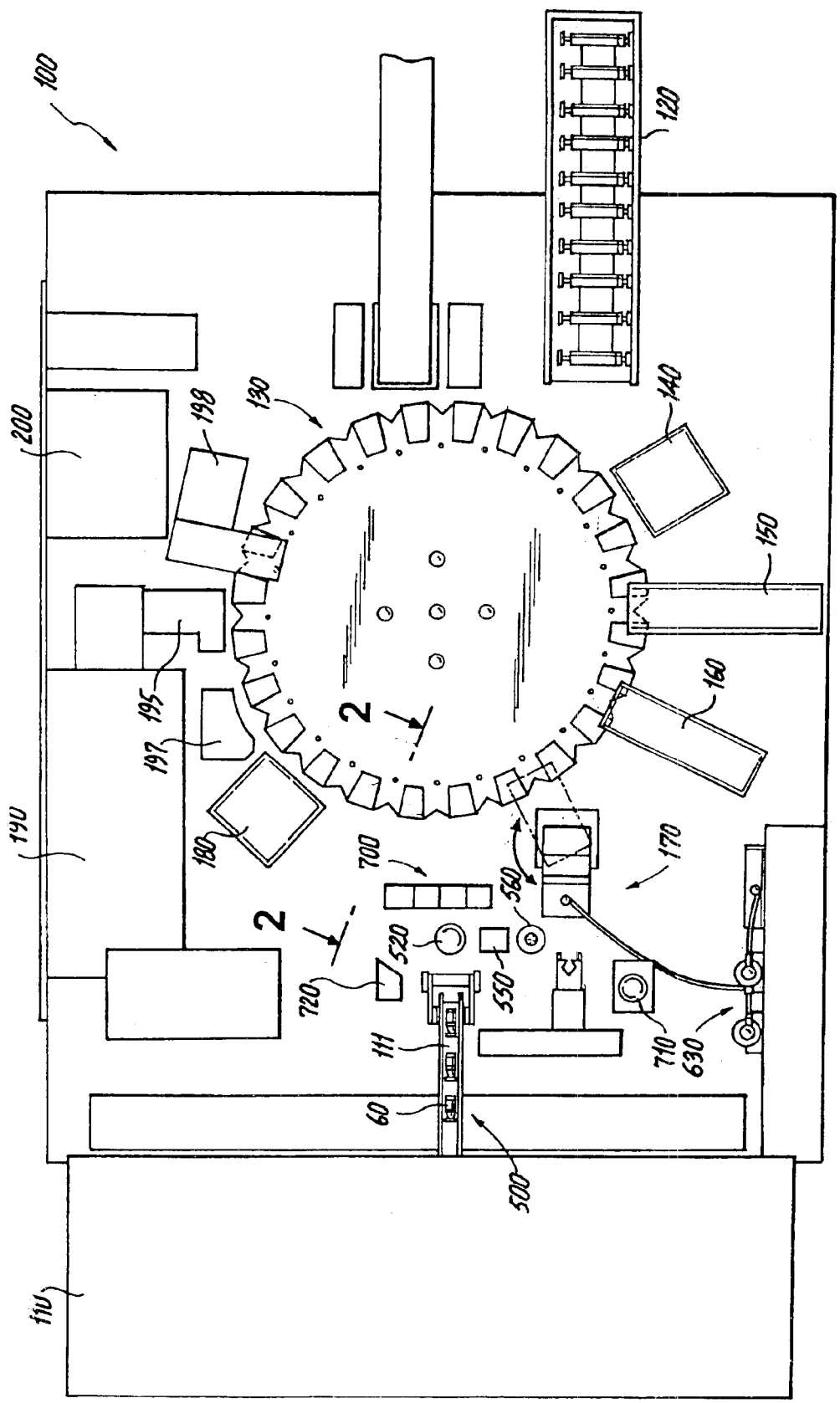
FIG. 2 is a diagrammatic plan view of an automated system for preparing a medication to be administered to a patient.

FIG. 2 is a schematic diagram illustrating one exemplary automated system, generally indicated at 100, for the preparation of a medication. The automated system 100 is divided into a number of stations where a specific task is performed based on the automated system 100 receiving user input instructions, processing these instructions and then preparing unit doses of one or more medications in accordance with the instructions. The automated system 100 includes a station 110 where medications and other substances used in the preparation process are stored. As used herein, the term "medication" refers to a medicinal preparation for administration to a patient. Often, the medication is initially stored as a solid, e.g., a powder, to which a diluent is added to form a medicinal composition. Thus, the station 110 functions as a storage unit for storing one or medications, etc. under proper storage conditions. Typically, medications and the like are stored in sealed containers, such as vials, that are labeled to clearly indicate the contents of each vial.

A first station 120 is a syringe storage station that houses and stores a number of syringes. For example, up to 500 syringes or more can be disposed in the first station 120 for storage and later use. The first station 120 can be in the form of a bin or the like or any other type of structure than can hold a number of syringes. In one exemplary embodiment, the syringes are provided as a bandolier structure that permits the syringes to be fed into the other components of the system 100 using standard delivery techniques, such as a conveyor belt, etc.

The system 100 also includes a rotary apparatus 130 for advancing the fed syringes from and to various stations of the system 100. A number of the stations are arranged circumferentially around the rotary apparatus 130 so that the syringe is first loaded at the first station 120 and then rotated a predetermined distance to a next station, etc. as the medication preparation process advances. At each station, a different operation is performed with the end result being that a unit dose of medication is disposed within the syringe that is then ready to be administered.

One exemplary type of rotary apparatus 130 is a multiple station cam-indexing dial that is adapted to perform material handling operations. The indexer is configured to have multiple stations positioned thereabout with individual nests for each station position. One syringe is held within one nest using any number of suitable techniques, including opposing spring-loaded fingers that act to clamp the syringe in its respective nest. The indexer permits the rotary apparatus 130 to be advanced at specific intervals.

At a second station 140, the syringes are loaded into one of the nests of the rotary apparatus 130. One syringe is loaded into one nest of the rotary apparatus 130 in which the syringe is securely held in place. The system 100 preferably includes additional mechanisms for preparing the syringe for use, such as removing a tip cap and extending a plunger of the syringe at a third station 150. At this point, the syringe is ready for use.

The system 100 also preferably includes a reading device (not shown) that is capable of reading a label disposed on the sealed container containing the medication. The label is read using any number of suitable reader/scanner devices, such as a bar code reader, etc., so as to confirm that the proper medication has been selected from the storage unit of the station 110. Multiple readers can be employed in the system at various locations to confirm the accuracy of the entire process. Once the system 100 confirms that the sealed container that has been selected contains the proper medication, the container is delivered to a fourth station 160 using an automated mechanism, such a robotic gripping device as will be described in greater detail. At the fourth station 160, the vial is prepared by removing the safety cap from the sealed container and then cleaning the exposed end of the vial. Preferably, the safety cap is removed on a deck of the automated system 100 having a controlled environment. In this manner, the safety cap is removed just-in-time for use.

The system 100 also preferably includes a fifth station (fluid transfer station) 170 for injecting or delivering a diluent into the medication contained in the sealed container and then subsequently mixing the medication and the diluent to form the medication composition that is to be disposed into the prepared syringe. At this fluid transfer station, the prepared medication composition is withdrawn from the container (i.e., vial) and is then delivered into the syringe. For example, a cannula can be inserted into the sealed vial and the medication composition then aspirated into a cannula set. The cannula is then withdrawn from the vial and is then rotated relative to the rotary apparatus 130 so that it is in line with (above, below, etc.) the syringe. The unit dose of the medication composition is then delivered to the syringe, as well as additional diluent if necessary or desired. The tip cap is then placed back on the syringe at a sixth station 180. A seventh station 190 prints and station 195 applies a label to the syringe and a device, such as a reader, can be used to verify that this label is placed in a correct location and the printing thereon is readable. Also, the reader can confirm that the label properly identifies the medication composition that is contained in the syringe. The syringe is then unloaded from the rotary apparatus 130 at an unloading station 200 and delivered to a predetermined location, such as a new order bin, a conveyor, a sorting device, or a reject bin. The delivery of the syringe can be accomplished using a standard conveyor or other type of apparatus. If the syringe is provided as a part of the previously-mentioned syringe bandolier, the bandolier is cut prior at a station 198 located prior to the unloading station 200.

Figure 3:
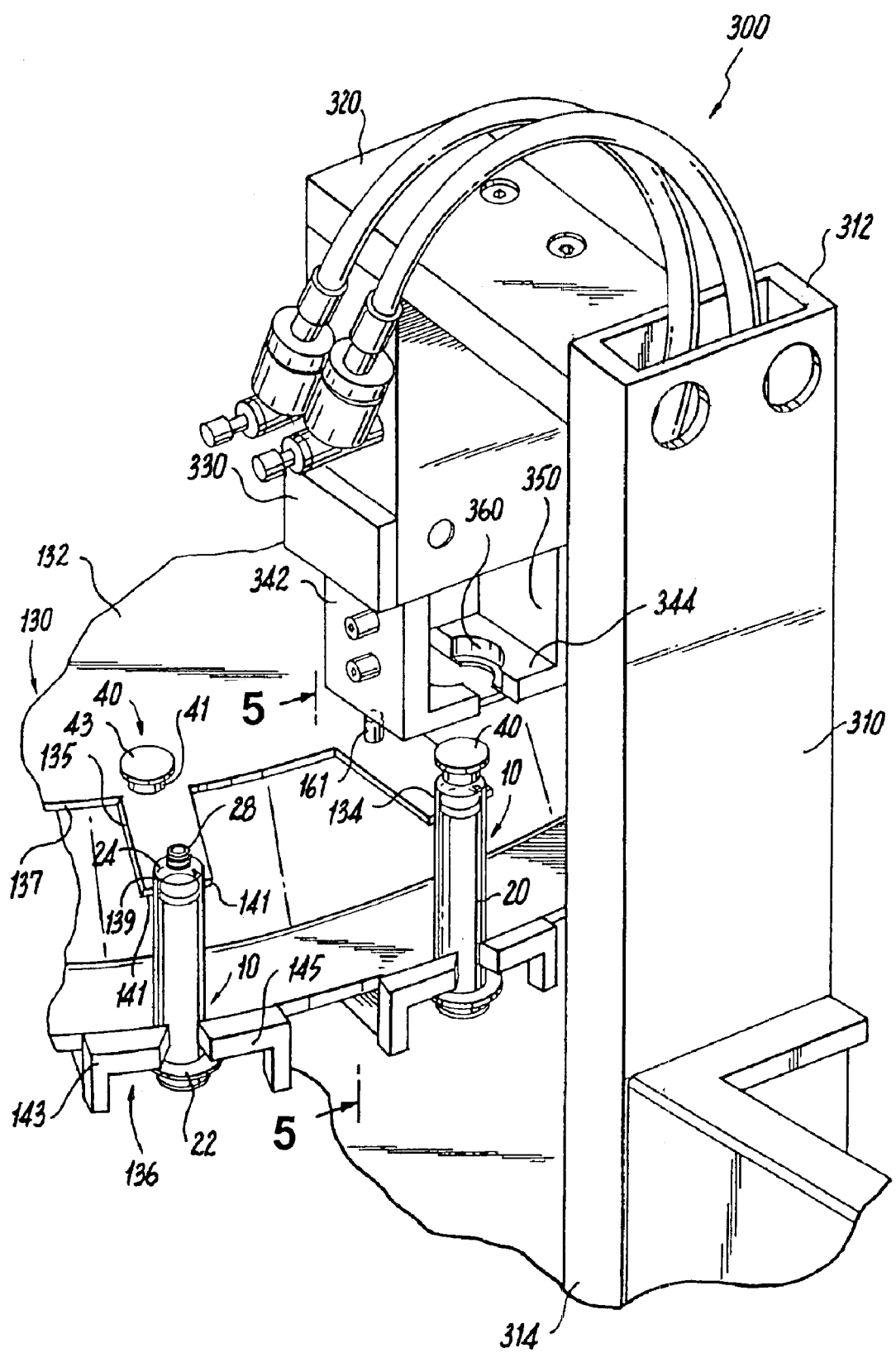
FIG. 3 is a local perspective view of an automated device for removing the safety tip cap from the syringe.

FIGS. 3 through 15 illustrate parts of the third station 150 for preparing a syringe, the fluid transfer station 170, and the sixth station 180 for preparing the syringe for later use. In other words, FIGS. 3–15 illustrate in more detail the stations and automated devices that are used in removal of the tip cap 40 from the barrel tip 28, the filling of barrel chamber 30 with medication and the replacement of the tip cap 40 on the barrel tip 28. FIG. 3 is a perspective view of an automated device 300 that removes the tip cap 40 from the barrel tip 28 as the syringe 10 is prepared for receiving a prescribed dose of medication as part of the third station 150 of the automated medication preparation system 100. The device 300 is a controllable device that is operatively connected to a control unit, such as a computer, which drives the device 300 to specific locations at selected times. The control unit can be a personal computer that runs one or more programs to ensure coordinated operation of all of the components of the system 100. The device 300 and other suitable devices described in greater detail in U.S. Ser. No. 10/426,910, which is hereby incorporated by reference in its entirety.

As previously mentioned, one exemplary rotary device 130 is a multiple station cam-indexing dial that is adapted to perform material handling operations. The dial 130 has an upper surface 132 and first and second retaining members 134, 136 for securely holding one syringe 10 in a releasable manner. More specifically, the first retaining member 134 locates the barrel 20 near the distal end 24 thereof and the second retaining member 136 grips and holds the barrel 20 near the proximal end 22 thereof. One exemplary first retaining member 134 includes an arm 135 that is integral to the upper surface 132 of the rotary device 130 and extends outwardly from a main peripheral edge 137 of the dial. The arm 135 has a notch 139 formed at a distal end thereof that is complementary in shape and size to the outer surface of the syringe 10 so that the syringe barrel 20 is received and held within the notch 139. The notch 139 is defined by a pair of opposing fingers 141, with the notch 139 being formed therebetween. The notch 139 is thus V-shaped in this exemplary embodiment.

The second retaining member 136 is configured to hold and retain the proximal end 22 of the barrel 20. The second retaining member 136 includes operable pivotable arms 143, 145 that pivot between an open position where the syringe 10 is free to be removed from the dial 130 and a closed position in which the syringe 10 is securely held on the dial 130. A shaped surface 151 also forms a part of the retaining member 136 and is disposed behind the pivotable arms 143, 145. The syringe 10 is disposed between the pivotable arms 143, 145 and the surface 151 and in the retained position, the pivotable arms 143, 145 are in the closed position and the syringe 10 is held securely between the pivotable arms 143, 145 and the surface 151. As will be described in greater detail hereinafter, the controller directs the pivotable arms 143, 145 to either the open or closed positions.

A post 161 is provided for holding the tip cap 40 after its removal to permit the chamber 30 to be filled with medication. One exemplary post 161 has a circular cross-section and is formed near or at the interface between the arm 135 and the dial 130. The post 161 can also be formed on the upper surface 132 of the dial 130. Thus, the precise location of the post 161 can vary so long as the post 161 is located where the tip cap 40 can sit without interfering with the operation of any of the automated devices and also the post 161 should not be unnecessarily too far away from the held syringe 10 since it is desired for the automated devices to travel a minimum distance during their operation to improve the overall efficiency of the system 100. The specific shape of the post 161 can likewise vary so long as the post 161 can hold the tip cap 40 so that it remains on the post 161 during the rotation of the dial 130 as the associated syringe 10 is advanced from one station to another station.

While in one exemplary embodiment, the syringes 10 are fed to the rotary device 130 as part of a syringe bandolier (i.e., multiple syringes 10 are disposed in series and interconnected by a web), it will be appreciated that the syringes 10 can be fed to the rotary device 130 in any number of other ways. For example, the syringes 10 can be fed individually into the rotary device 130 from a loose supply of syringes 10.

The automated device 300 is a robotic device and preferably, the automated device 300 is a linear actuator with a gripper. The device 300 has a vertical base 310 which is adjustable in at least several directions. For example, the vertical base 310 has an independent reach (y axis) and vertical axis (x axis) which provides part of the flexibility and motion control that is desirable for the device 300. The vertical base 310 has an upper end 312 and an opposing lower end 314 which is operatively coupled to other movable components to permit the vertical base 310 to move in an up/down direction along the x axis and in lateral directions along the y axis. The upper end 312 is connected to a horizontal support member 320 that extends outwardly away from the vertical base 310. In one exemplary embodiment, the lower end 314 is disposed between two support beams that are part of a robotic device and are moved in a number of different directions, including along the x axis and the y axis.

A block member 330 is connected to the horizontal support member 320 and more specifically, the block member 330 is disposed on an underside of the horizontal support member 320 so that it is spaced away from the vertical base 310. The exemplary block member 330 has a block-like shape and is connected to the underside of the horizontal support member 320 by one or more connectors that can be in the form of support columns, etc.

The device 300 has first and second positionable gripping arms 340, 350 which are adjustable in at least one direction and which are coupled to and extend downwardly from the block member 330. For example, each of the gripping arms 340, 350 is movable at least in a direction along the y axis which provide the flexibility and motion control that is desirable in the present system 100. The gripping arms 340, 350 are programmed to work together in tandem so that both arms 340, 350 are driven to the same location and the same time.

The block member 330 can house some of the electronic components and the like that permit the gripping arms 340, 350 to move between the open and closed positions. The coupling between the block member 330 and the gripping arms 340, 350 is such that the gripping arms 340, 350 have the necessary degree of movement to permit the opening and closing thereof.

Each of the gripping arms 340, 350 is a generally L-shaped member that is formed of a vertical section 342 and a horizontal gripping section 344 that extends outwardly from one end of the vertical section 342. The gripping section 344 has a cut-out or notch 360 formed therein for receiving and gripping a section of the tip cap 40 of the syringe 10. Accordingly, the notch 360 has a complementary shape as the shape of the tip cap 40. One exemplary notch 360 has a generally semi-circular shape and it seats against approximately ½ of the outer circumferential surface of the tip cap 40. By being movable along at least the y axis, the gripping arms 340, 350 can be positioned between an open position in which the opposing gripping sections 344 of the arms 340, 350 are spaced apart from one another a sufficient distance to permit the tip cap 40 to be received therebetween.

The tip cap 40 has a base section 41 and a flange 43 that has a diameter that is greater than the diameter of the base section 41. The gripping sections 344 of the arms 340, 350 are contoured to seat against the outer circumferential surface of the base section 41 of the tip cap 40. In the closed position, the gripping sections 344 of the arms 340, 350 are brought together so that they either seat against one another or are in very close proximity to one another. When the gripping sections 344 come together in the closed position, the notches 360 define a complete circular opening that has a diameter about equal to or slightly less than the diameter of the base section 41 of the tip cap 40, thereby permitting the tip cap 40 to nest within the gripping sections 344.

In FIG. 3, a first open position of the gripping arms 340, 350 is illustrated with the gripping sections 344 being spaced sufficiently from one another so as to permit the tip cap 40 to be freely disposed between the gripping sections 344. Using a control unit 370 (e.g., a programmable actuator, microprocessor, etc.), the gripping arms 340, 350 are driven to the first position shown in FIG. 4. The control unit 370 instructs the device 300 to perform an operation where the tip cap 40 is gripped and removed by the device 300. When such an operation is performed, the vertical base 310 is driven inwardly toward the dial 130 and relative to the syringe 10 so that the gripping arms 340, 350 are positioned over the tip cap 40 that is disposed on top of the syringe 10. The vertical base 310 is then driven downward until the gripping arms 340, 350 are disposed around the tip cap 40. In other words, the tip cap 40 is disposed between the gripping section 344 of the opposing arms 340, 350 and more specifically, the gripping sections 344 are disposed adjacent the base section 41 of the tip cap 40 underneath the flange 43 with the notches 360 being aligned with the outer surface of the base section 41. An actuator or the like of the device 300 is then activated causing the gripping arms 340, 350 to move inwardly toward one another until the gripping sections 344 seat against the outer surface of the base section 41 of the tip cap 40. In this closed position, the gripping arms 340, 350 apply a force against the base section 41 so that the tip cap 40 is securely held by the gripping sections 344. When the gripping arms 340, 350 are driven to the closed position, the gripping sections 344 seat against one another and the notches 360 align such that the gripping sections 344 substantially encircle the base section 41.

The apparatus 300 can be driven in any number of different ways that are known and suitable for this intended use. For example, the apparatus 300 can be pneumatically based according to one exemplary embodiment and as shown in FIG. 3. In this embodiment, a number of pneumatic conduits are provided for moving the gripping arms 340, 350.

After the tip cap 40 is nested within the gripping sections 344, the control unit 370 directs the vertical base 310 upward and this motion causes the tip cap 40 to be displaced from the barrel tip 28 as shown in phantom in FIG. 5. After the tip cap 40 is freed from the barrel tip 28, it remains held between the gripping sections 344 of the opposing arms 340, 350. The vertical base 310 is then driven more inward, as indicated by arrow 311, toward the dial 130 until the held tip cap 40 is positioned over the post 161. Once the tip cap 40 is disposed over the post 161, the controller 370 instructs the vertical base 310 to move downwardly so that the post 161 is disposed within a hollow interior of the tip cap 40. The actuator is then activated causing the gripping arms 340, 350 to move to the open position, thereby releasing the tip cap 40 as shown in FIG. 5. Because the tip cap 40 sits on the post 161, its movement is restricted after the gripping arms 340, 350 release their gripping action therefrom and the tip cap 40 remains seated on the post 161 as the rotary device 130 advances to deliver the uncapped syringe 10 to another station. The device 300 then is returned to its initial position, the dial 130 is advanced and the operation is repeated with the device 300 gripping and removing one tip cap 40 from the next capped syringe 10.

Figure 6:
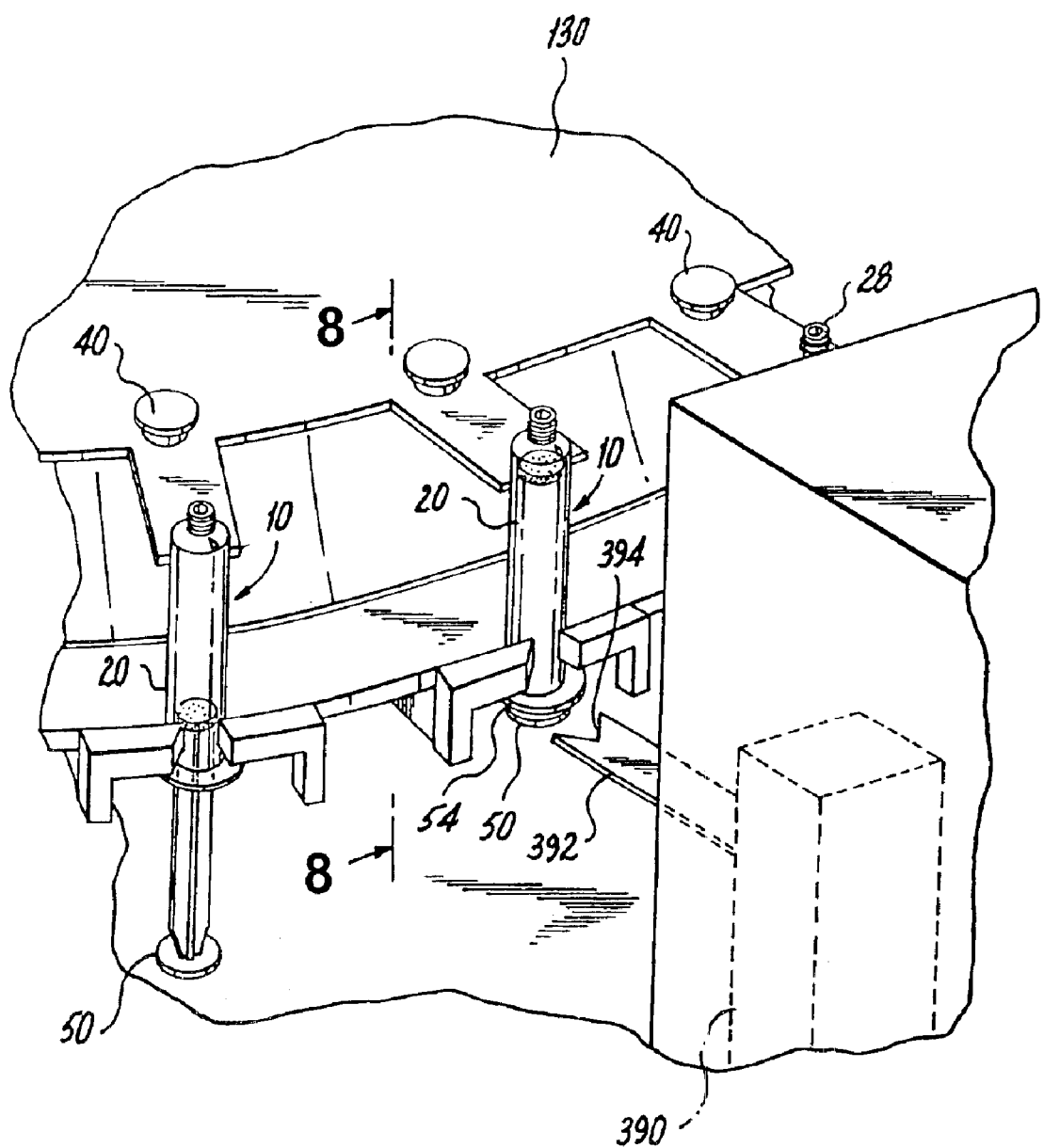
FIG. 6 is a local perspective view of a device for extending a plunger of the syringe.
Figure 8:
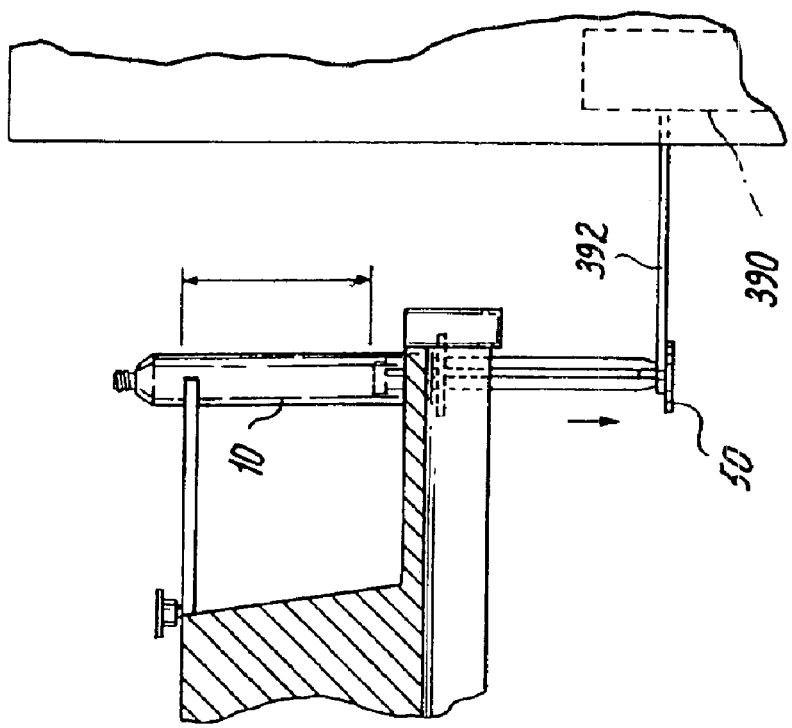
FIG. 8 is a sectional elevation view of the device of FIG. 6 showing extension of the plunger.
Figure 7:
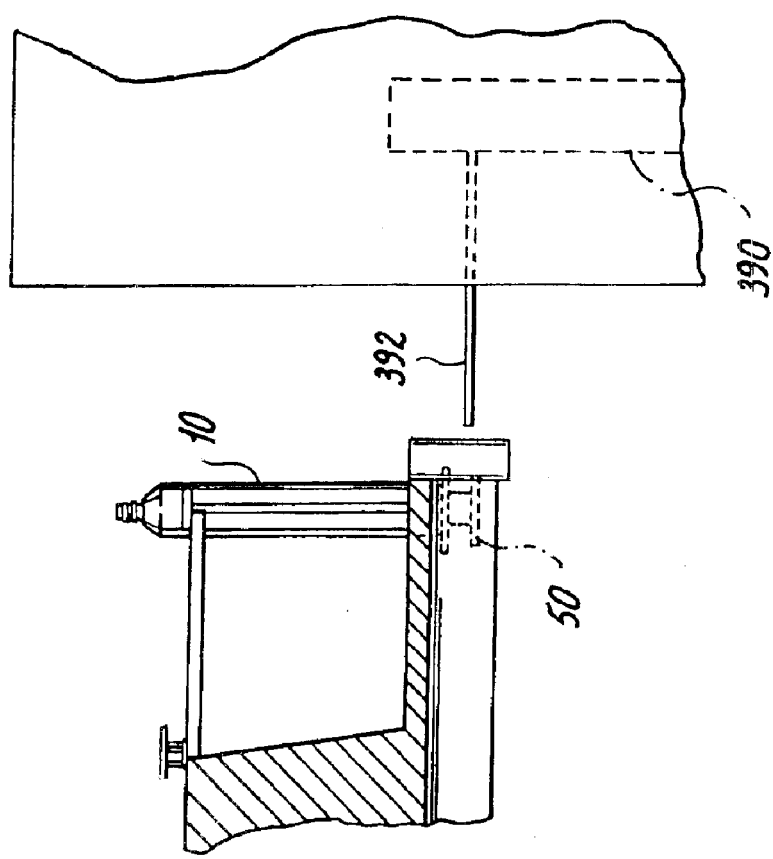
FIG. 7 is a sectional elevation view of the device of FIG. 6 prior to engaging the plunger.
Figure 9:
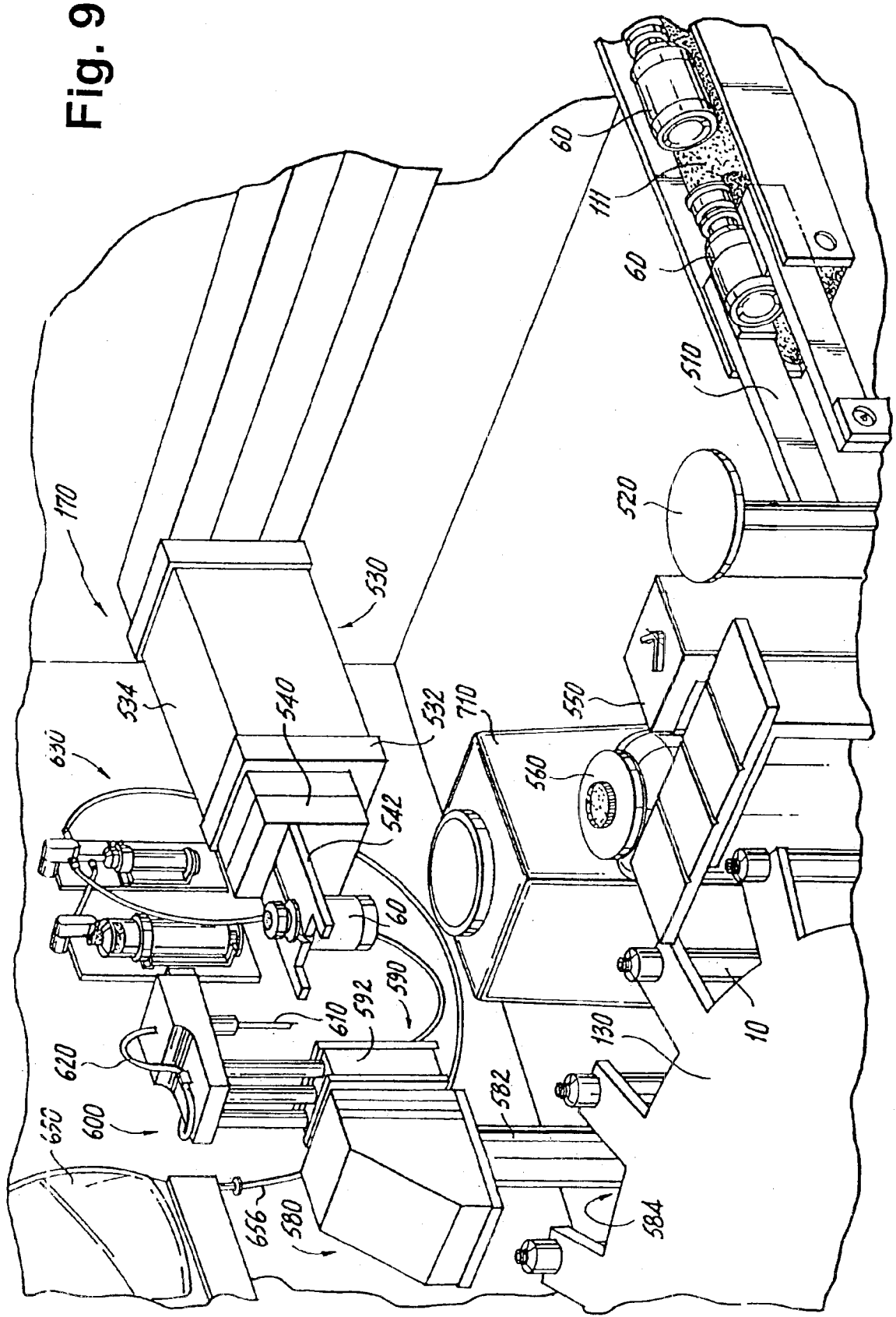
FIG. 9 is a local perspective view of fluid transfer and vial preparation equipment in a fluid transfer area of the automated system.

Now referring to FIGS. 6–8, the system 100 also includes a device 400 for extending the plunger 50 of one uncapped syringe 10 after it has had its tip cap 40 removed therefrom. For ease of illustration, the device 400 as well as the device 300 are described as being part of the third station 150 of the system 100. The device 400 extends the plunger 50 so that the syringe 10 can receive a desired dose based upon the particular syringe 10 being used and the type of application (e.g., patient's needs) that the syringe 10 is to be used for. The device 400 can have any number of configurations so long as it contains a feature that is designed to make contact with and withdraw the plunger 50. In one exemplary embodiment, the automated device 400 is a robotic device and preferably, the automated device 400 is a linear actuator with a gripper. For example, one exemplary device 400 is a mechanical device that has a movable gripper 410 that includes a gripping edge 420 that engages the flange 54 of the plunger 50, as shown in FIG. 7, and then the gripper 410 is moved in a downward direction causing the plunger 50 to be moved a predetermined amount as shown in FIG. 8. For example, the gripper 410 can be the part of an extendable/retractable arm that includes the gripping edge 420 for engaging the syringe 10 above the plunger flange 54. When an actuator or the like causes the gripper 410 to move in a downward direction, the gripping edge 420 seats against the flange 54 and further movement of the gripper 410 causes the extension of the plunger 50. Once the plunger 50 has been extended the prescribed distance, the gripper 410 moves laterally away from the plunger 50 so that the interference between the flange 54 of the plunger 50 and the gripping edge 420 no longer exits. In other words, the gripper 410 is free of engagement with the plunger 50 and can therefore be positioned back into its initial position by being moved laterally and/or in an up/down direction (e.g., the gripper 410 can move upward to its initial position). Another exemplary plunger extending device is described in commonly assigned U.S. patent application Ser. No. 10/457, 066, which is hereby incorporated by reference in its entirety.

Thus, the device 400 complements the device 300 in getting the syringe 10 ready for the fluid transfer station at which time, a prescribed amount of medication is dispensed into the chamber 30 of the barrel 20 as will be described in greater detail hereinafter.

The device 400 is part of the overall programmable system and therefore, the distance that the gripper 410 corresponds to a prescribed movement of the plunger 50 and a corresponding increase in the available volume of the chamber 30 of the barrel 20. For example, if the prescribed unit dose for a particular syringe 10 is 8 ml then the controller instructs the device 400 to move the gripper 410 a predetermined distance that corresponds with the plunger 50 moving the necessary distance so that the volume of the barrel chamber 30 is at least 8 ml. This permits the unit dose of 8 ml to be delivered into the barrel chamber 30.

In one example, after the syringe 10 has been prepared by removing the tip cap 40 and extending the plunger 50 a prescribed distance, the syringe 10 is then delivered to a fluid transfer station where a fluid transfer device 500 prepare and delivers the desired amount of medication.

Now turning to FIGS. 2 and 9–20 in which a drug preparation area is illustrated in greater detail to show the individual components thereof. More specifically, a drug transfer area 500 is illustrated and is located proximate the rotary dial 130 so that after one drug vial 60 is prepared, the contents thereof can be easily delivered to syringes 10 that are securely held in nested fashion on the rotary dial 130. As previously mentioned, drug vials 60 are stored typically in the storage cabinet 110 and can be in either liquid form or solid form. A driven member, such as a conveyor belt 111 delivers the drug vial 60 from the cabinet 110 to a first pivotable vial gripper mechanism 510 that receives the vial 60 in a horizontal position and after gripping the vial with arms or the like, the mechanism 510 pivots upright so that the vial 60 is moved a vertical position relative to the ground and is held in an upright manner.

The mechanism 510 is designed to deliver the vial 60 to a rotatable pedestal 520 that receives the vial 60 once the grippers of the mechanism 510 are released. The vial 60 sits upright on the pedestal 520 near one edge thereof that faces the mechanism 510 and is then rotated so that the vial 60 is moved toward the other side of the pedestal 520. As the pedestal rotates, the vial 60 is scanned and a photoimage thereof is taken and the vial 60 is identified. If the vial 60 is not the correct vial, then the vial 60 is not used and is discarded using a gripper device that can capture and remove the vial 60 from the pedestal before it is delivered to the next processing station. The central control has a database that stores all the identifying information for the vials 60 and therefore, when a dose is being prepared, the controller knows which vial (by its identifying information) is to be delivered from the cabinet 110 to the pedestal 520. If the scanning process and other safety features does not result in a clear positive identification of the vial as compared to the stored identifying information, then the vial is automatically discarded and the controller will instruct the system to start over and retrieve a new vial.

If the vial 60 is identified as being the correct vial, then a vial gripper device 530 moves over to the pedestal for retrieving the vial 60. The vial gripper device 530 is configured to securely grip and carry the vial in a nested manner to the next stations as the drug is prepared for use. For example, the device 530 can include a vertical base 532 that is operatively coupled to a moveable base portion 534 that can ride within tracks to permit the device 530 to move not only in forward-rearward directions but also in a side-to-side manner. At a distal end of the vertical base 532, a gripper unit 540 is provided and is operatively coupled to the vertical base 532 so that the gripper unit 540 can move in an up-and-down direction. For example, the gripper unit 540 can be pneumatically supported on the vertical base 532 so that activation of the pneumatic mechanism causes either up or down movement of the gripper unit 540 relative to the vertical base 532. The gripper unit 540 includes a pair of grippers or arms 542 that are positionable between closed and open positions with the vial 60 being captured between the arms 542 in the closed position in such a manner that the vial 60 can be securely moved and even inverted and shaken without concern that the vial 60 will become dislodged and fall from the arms 542. The arms 542 thus have a complementary shape as the vial 60 so that when the arms 542 close, they engage the vial and nest around a portion (e.g., neck portion) of the vial 60 resulting in the vial 60 being securely captured between the arms 542. As with some of the other components, the arms 542 can be pneumatically operated arms.

In order to retrieve the vial 60 from the pedestal 520, the device 530 is driven forward and then to one side so that it is position proximate the pedestal 520. The gripper unit 540 is then moved downward so that the arms 542, in their open position, are spaced apart with the vial 60 being located between the open arms 542. The gripper unit 540 is then actuated so that the arms 542 close and capture the vial 60 between the arms 542. Next the gripper unit 540 is moved upward and the device 530 is driven back to the opposite side so as to introduce the vial 60 to the next station. The vial 60 is also inverted by inversion of the gripper unit 540 so that the vial 60 is disposed upside down.

The inverted vial 60 is then delivered to a station 550 where the vial 60 is prepared by removing the safety cap from vial 60. This station 550 can therefore be called a vial decapper station. Any number, of devices can be used at station 550 to remove the safety cap from the vial. For example, several exemplary decapper devices are disclosed in commonly-assigned U.S. Pat. No. 6,604,903 which is hereby incorporated by reference in its entirety. After the vial 60 is decapped, the vial is then delivered, still in the inverted position, to a cleaning station 560 where the exposed end of the vial is cleaned. For example, underneath the removed vial safety cap, there is a septum that can be pierced to gain access to the contents of the vial. The cleaning station 560 can be in the form of a swab station that has a wick saturated with a cleaning solution, such as an alcohol. The exposed area of the vial 60 is cleaned by making several passes over the saturated wick which contacts and baths the exposed area with cleaning solution. After the vial 60 is cleaned at the station 560, the gripper unit 540 rotates so that the vial 60 is returned to its upright position and remains held between the gripper arms 542.

The device 530 then advances forward to a fluid transfer station 570. The fluid transfer station 570 is an automated station where the medication (drug) can be processed so that it is in a proper form for injection into one of the syringes 10 that is coupled to the rotary dial 130. When the vial 60 contains only a solid medication and it is necessary for a diluent (e.g., water or other fluid) to be added to liquify the solid, this process is called a reconstitution process. Alternatively and as will be described in detail below, the medication can already be prepared and therefore, in this embodiment, the fluid transfer station is a station where a precise amount of medication is simply aspirated or withdrawn from the vial 60 and delivered to the syringe 10.

Figure 14:
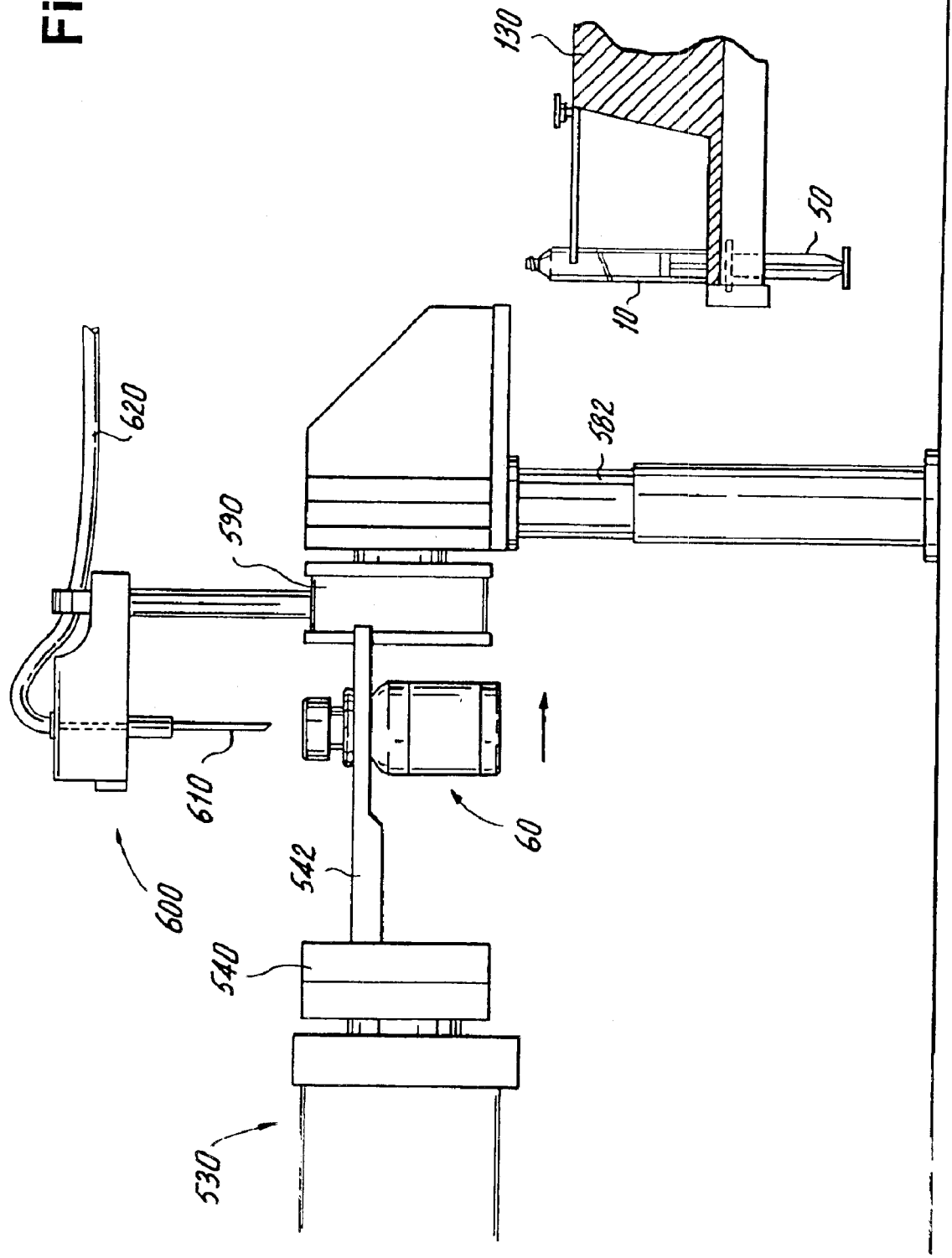
FIG. 14 is a side elevation view of a fluid transfer device in a first position where a cannula unit is in an extended position and the vial gripper device moves the vial into a fluid transfer position.

For purpose of illustration, the reconstitution process is first described. After having been cleaned, the vial 60 containing a prescribed amount of solid medication is delivered in the upright position to the fluid transfer station 570 by the device 530 as shown in FIG. 14. As will be appreciated, the device 530 has a wide range of movements in the x, y and z directions and therefore, the vial 60 can easily be moved to a set fluid transfer position. At this position, the vial 60 remains upright and a fluid transfer device 580 is brought into position relative to the vial 60 so that a fluid transfer can result therebetween. More specifically, the fluid transfer device 580 is the main means for both discharging a precise amount of diluent into the vial 60 to reconstitute the medication and also for aspirating or withdrawing the reconstituted medication from the vial 60 in a precise, prescribed amount. The device 580 is a controllable device that is operatively connected to a control unit, such as a computer, which drives the device 580 to specific locations at selected times. The control unit can be a personal computer that runs one or more programs to ensure the coordinated operation of all of the components of the system 100.

Figure 15:
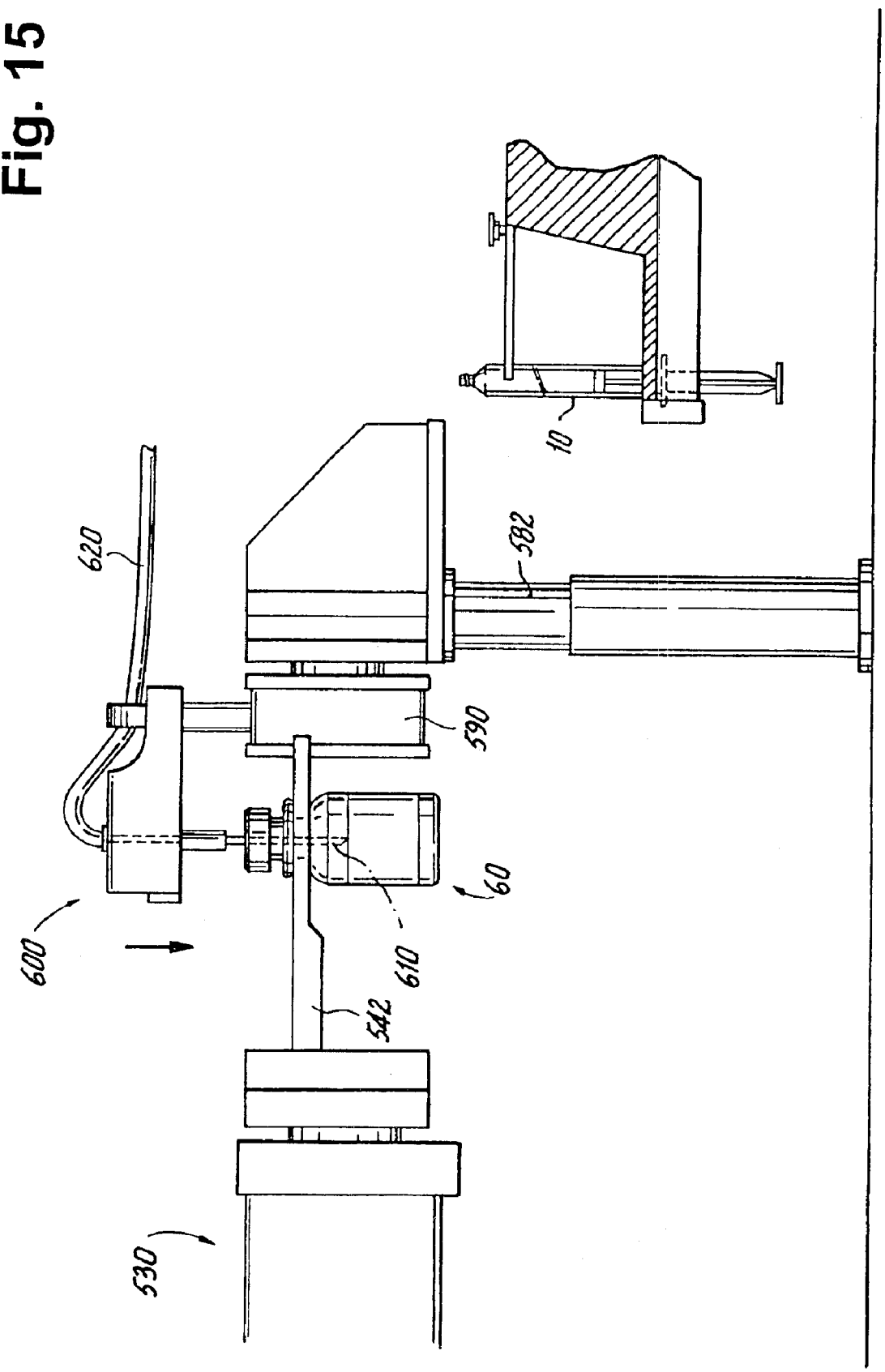
FIG. 15 is a side elevation view of the fluid transfer device in a second position in which the cannula is rectracted into the vial to permit transfer either to or from the vial.

As illustrated in FIGS. 2 and 9–20, one exemplary fluid transfer device 580 includes a vertical base section 582 that is rotatably mounted to a base 584 so that the device 580 can rotate between the fluid transfer position to the rotary device 130 where the medication is discharged into the syringes 10. The base 584 can be mounted so that it can move in both the x and y directions. Near a distal end of the base 584, a rotatable cannula unit 590 is operatively and rotatably coupled to the base 584 to permit the cannula unit 590 a degree of rotation relative to the base 584. For example, the cannula unit 590 can include a vertical housing 592 that is rotatably coupled to the base 584 between the ends thereof. At an upper end 594 of the housing 592, a cannula housing 600 is operatively coupled thereto such that the cannula housing 600 can be independently moved in a controlled up and down manner so to either lower it or raise it relative to the vial 60 in the fluid transfer position. For example, the cannula housing 600 can be pneumatically operated and therefore can includes a plurality of shafts 602 which support the cannula housing 600 and extend into an interior of the vertical housing 592 such that when the device is pneumatically operated, the shafts 602 can be driven either out of or into the housing 592 resulting in the cannula housing 600 either being raised or lowered, respectively, as shown in FIGS. 14 and 15.

At one end of the cannula housing 600 opposite the end that is coupled to the vertical housing 592, the cannula housing 600 includes a cannula 610. The cannula 610 has one end 612 that serves to pierce the septum of the vial 60 and an opposite end 614 that is connected to a main conduit 620 that serves to both deliver diluent to the cannula 610 and ultimately to the vial 60 and receive aspirated medication from the vial 60. Preferably, the cannula 610 is of the type that is known as a vented cannula which is vented to atmosphere as a means for eliminating any dripping or spattering of the medication during an aspiration process. More specifically, the use of a vented needle to add (and withdraw) the fluid to the vial overcomes a number of shortcoming associated with cannula fluid transfer and in particular, the use of this type of needle prevents backpressure in the vial (which can result in blow out or spitting or spraying of the fluid through the piercing hole of the cannula). The venting takes place via an atmospheric vent that is located in a clean air space and is formed in a specially designed hub that is disposed over the needle. By varying the depth that the needle penetrates the vial, the user can control whether the vent is activated or not. It will be appreciated that the venting action is a form of drip control (spitting) that may otherwise take place.

Moreover, the cannula 610 is also preferably of the type that is motorized so that the tip of the cannula 610 can move around within the vial 60 so that cannula 610 can locate and aspirate every last drop of the medication. In other words, the cannula 610 itself is mounted within the cannula unit 590 so that it can move slightly therein such that the tip moves within the vial and can be brought into contact with the medication wherever the medication may lie within the vial 60. Thus, the cannula 610 is driven so that it can be moved at least laterally within the vial 60.

An opposite end of the main conduit 620 is connected to a fluid pump system 630 that provides the means for creating a negative pressure in the main conduit 620 to cause a precise amount of fluid to be withdrawn into the cannula 610 and the main conduit 620 as well as creating a positive pressure in the main conduit 620 to discharge the fluid (either diluent or medication) that is stored in the main conduit 620 proximate the cannula 610. In the illustrated embodiment, the fluid pump system 630 includes a first syringe 632 and a second syringe 634, each of which has a plunger or the like 638 which serves to draw fluid into the syringe or expel fluid therefrom. The main difference between the first and second syringes 632, 634 is that the amount of fluid that each can hold. In other words, the first syringe 632 has a larger diameter barrel and therefore has increased holding capacity relative to the second syringe 634. As will be described in detail below, the first syringe 632 is intended to receive and discharge larger volumes of fluid, while the second syringe 634 performs more of a fine tuning operation in that it precisely can receive and discharge small volumes of fluid.

The syringes 632, 634 are typically mounted so that an open end 636 thereof is the uppermost portion of the syringe and the plunger 638 is disposed so that it is the lowermost portion of the syringe. Each of the syringes 632, 634 is operatively connected to a syringe driver, generally indicated at 640, which serves to precisely control the movement of the plunger 638 and thus precisely controls the amount (volume) of fluid that is either received or discharged therefrom. More specifically, the driver 640 is mechanically linked to the plunger 638 so that controlled actuation thereof causes precise movements of the plunger 638 relative to the barrel of the syringe. In one embodiment, the driver 640 is a stepper motor that can precisely control the distance that the plunger 638 is extended or retracted, which in turn corresponds to a precise volume of fluid being aspirated or discharged. Thus, each syringe 632, 634 has its own driver 640 so that the corresponding plunger 638 thereof can be precisely controlled and this permits the larger syringe 632 to handle large volumes of fluid, while the smaller syringe 634 handles smaller volumes of fluid. As is known, stepper motors can be controlled with a great degree of precision so that the stepper motor can be only be driven a small number of steps which corresponds to the plunger 638 being moves a very small distance. On the other hand, the stepper motor can be driven a large number of steps which results in the plunger 638 being moved a much greater distance. The drivers 640 are preferably a part of a larger automated system that is in communication with a master controller that serves to monitor and control the operation of the various components. For example, the master controller calculates the amount of fluid that is to be either discharged from or aspirated into the cannula 610 and the main conduit 620 and then determines the volume ratio as to how much fluid is to be associated with the first syringe 632 and how much fluid is to be associated with the second syringe 634. Based on these calculations and determinations, the controller instructs the drivers 640 to operate in a prescribed manner to ensure that the precise amount of volume of fluid is either discharged or aspirated into the main conduit 620 through the cannula 610.

The open end 636 of each syringe 632, 634 includes one or more connectors to fluidly couple the syringe 632, 634 with a source 650 of diluent and with the main conduit 620. In the illustrated embodiment, the first syringe 632 includes a first T connector 660 that is coupled to the open end 636 and the second syringe 634 includes a second T connector 662 that is coupled to the open end 636 thereof. Each of the legs of the T connectors 660, 662 has an internal valve mechanism or the like 670 that is associated therewith so that each leg as well as the main body that leads to the syringe itself can either be open or closed and this action and setting is independent from the action at the other two conduit members of the connector. In other words and according to one preferred arrangement, the valve 670 is an internal valve assembly contained within the T connector body itself such that there is a separate valve element for each leg as well as a separate valve element for the main body. It will be appreciated that each of the legs and the main body defines a conduit section and therefore, it is desirable to be able to selectively permit or prevent flow of fluid in a particular conduit section.

In the illustrated embodiment, a first leg 661 of the first T connector 660 is connected to a first conduit 656 that is connected at its other end to the diluent source 650 and the second leg 663 of the first T connector 660 is connected to a connector conduit (tubing) 652 that is connected at its other end to the first leg of the second T connector 662 associated with the second syringe 634. A main body 665 of the first T connector 660 is mated with the open end 636 of the first syringe 632 and defines a flow path thereto. The connector conduit 652 thus serves to fluidly connect the first and second syringes 632, 634. As previously mentioned, the valve mechanism 670 is preferably of the type that includes three independently operable valve elements with one associated with one leg 661, one associated with the other leg 663 and one associated with the main body 665.

With respect to the second T connector 662, a first leg 667 is connected to the connector conduit 652 and a second leg 669 is connected to a second conduit 658 that is connected to the main conduit 620 or can actually be simply one end of the main conduit. A main body 671 of the second T connector 662 is mated with the open end 636 of the second syringe 634. As with the first T connector 660, the second T connector 662 includes an internal valve mechanism 670 that is preferably of the type that includes three independently operable valve elements with one associated with one leg 667, one associated with the other leg 669 and one associated with the main body 671.

Figure 10:
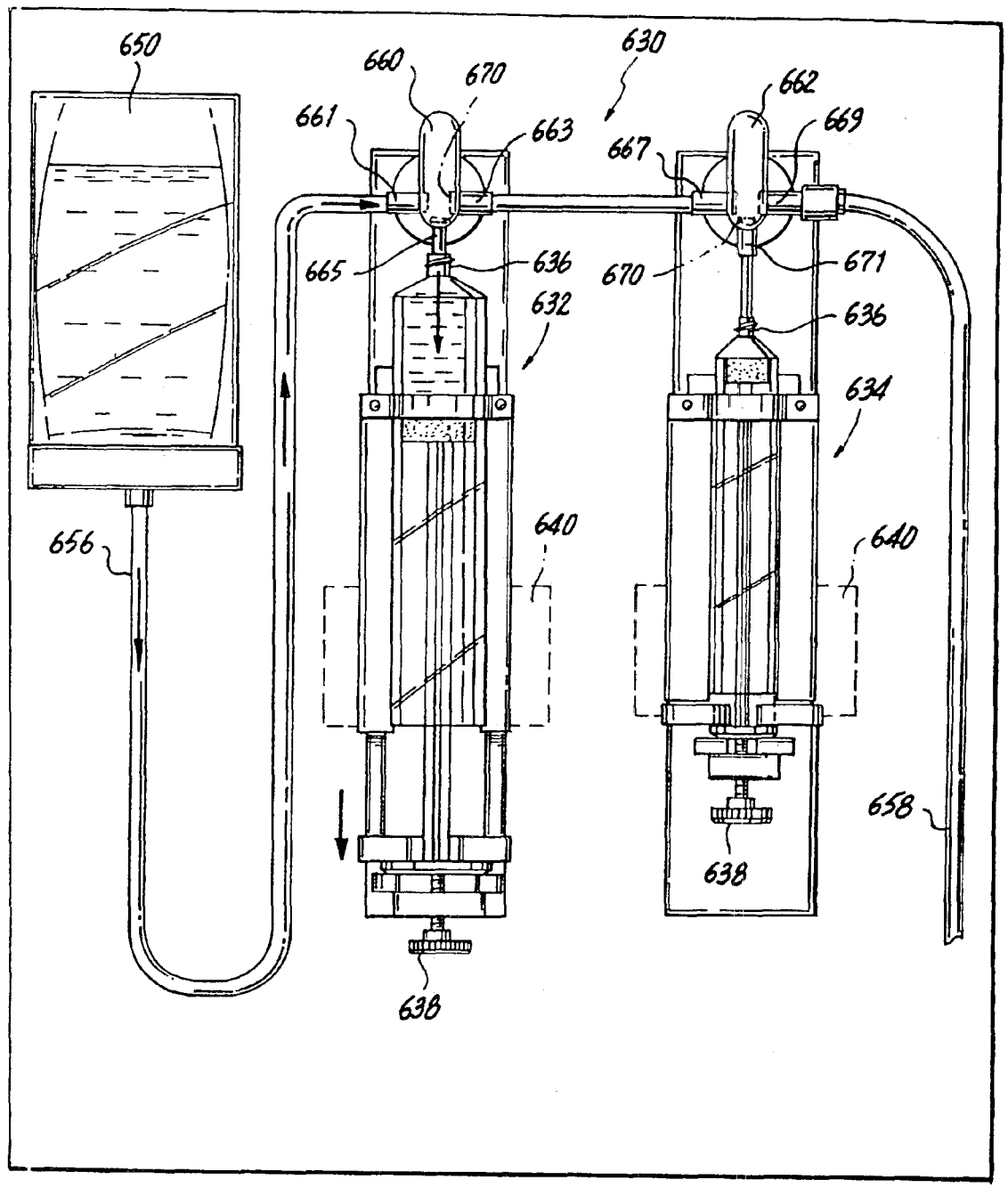
FIG. 10 is a side elevation view of a fluid pump system that that is located in the fluid transfer area shown in a first position for withdrawing diluent to one syringe.

The operation of the fluid pump system 630 is now described with reference to FIGS. 10–13. If the operation to be performed is a reconstitution operation, the valve 670 associated with the second leg 669 is first closed so that the communication between the syringes and the main conduit 620 is restricted. The valve element 670 associated with first leg 661 of the T connector 660 is left open so that a prescribed amount of diluent can be received from the source 650. The valve element associated with the second leg 663 of the T connector 660 is initially closed so that the diluent from the diluent source 650 is initially drawn into the first syringe 630 and the valve element associated with the main body 665 is left open so that the diluent can flow into the first syringe 632. The driver 640 associated with the first syringe 632 is then actuated for a prescribed period of time resulting in the plunger 638 thereof being extended a prescribed distance. As previously mentioned, the distance that the driver 640 moves the corresponding plunger 638 is directly tied to the amount of fluid that is to be received within the syringe 632. The extension of the plunger 638 creates negative pressure in the first syringe 632, thereby causing diluent to be drawn therein. This is shown in FIG. 10.

Figure 11:
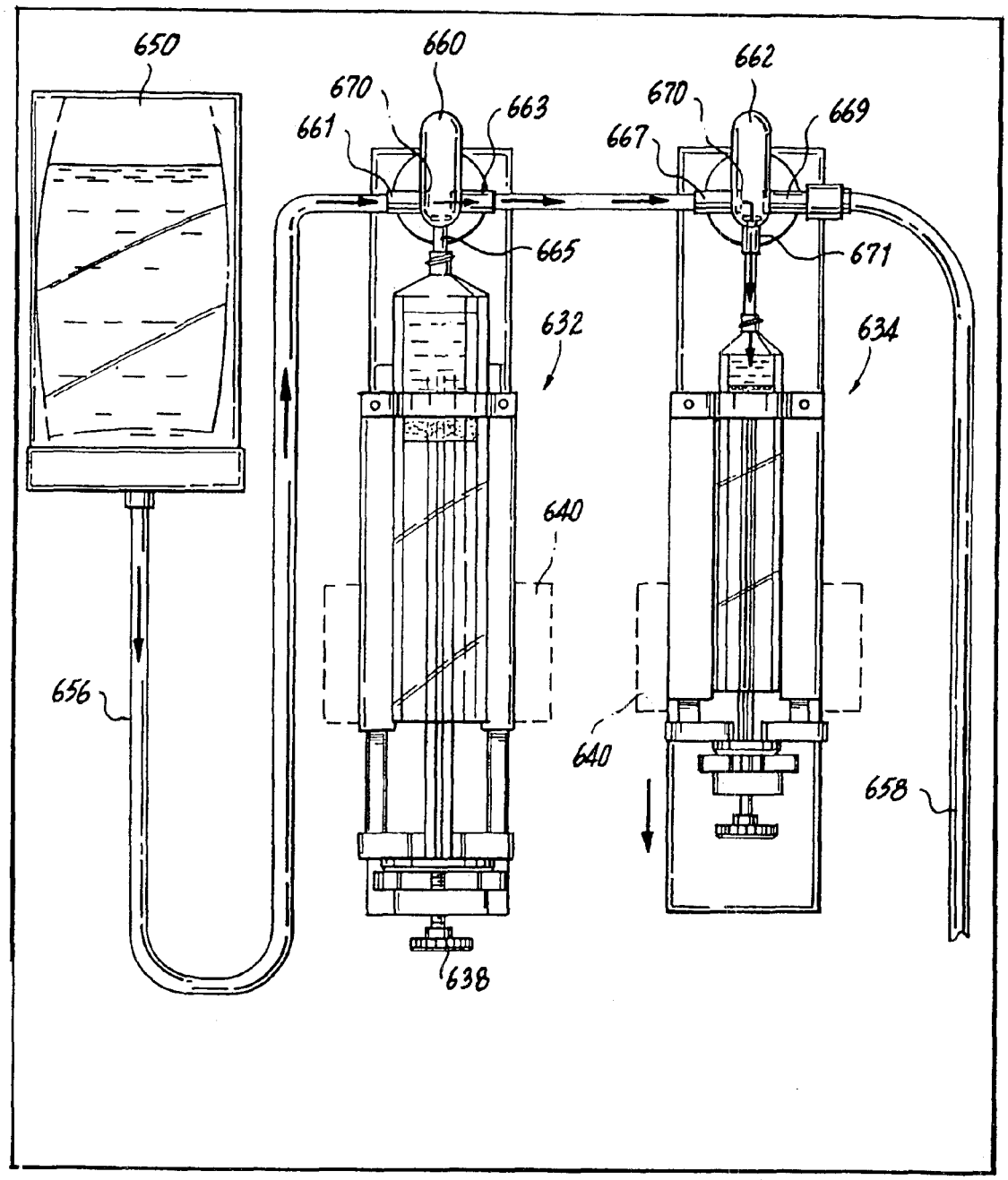
FIG. 11 is a side elevation view of the fluid pump system shown in a second position for withdrawing diluent to another syringe.

Once the prescribed amount of fluid is received in the first syringe 632, the valve element associated with the main body 665 of the T connector 660 is closed and the valve element associated with the second leg 663 is open, thereby permitting flow from the first T connector 660 to the second T connector 662 as shown in FIG. 11. At the same time, the valve element associated with the first leg 667 and the main body 671 of the second T connector 662 are opened (with the valve element associated with the second leg 669 being kept closed).

The driver 640 associated with the second syringe 634 is then actuated for a prescribed period of time resulting in the plunger 638 thereof being extended a prescribed distance which results in a precise, prescribed amount of fluid being drawn into the second syringe 634. The extension of the plunger 638 creates negative pressure within the barrel of the second syringe 634 and since the second T connector 662 is in fluid communication with the diluent source 650 through the first T connector 660 and the connector conduit 652, diluent can be drawn directly into the second syringe 632. The diluent is not drawn into the first syringe 660 since the valve element associated with the main body 665 of the first T connector 660 is closed.

Thus, at this time, the first and second syringes 632, 634 hold in total at least a prescribed volume of diluent that corresponds to at least the precise volume that is to be discharged through the cannula 610 into the vial 60 to reconstitute the medication contained therein.

It will be understood that all of the conduits, including those leading from the source 650 and to the cannula are fully primed with diluent prior to performing any of the above operations.

Figure 12:
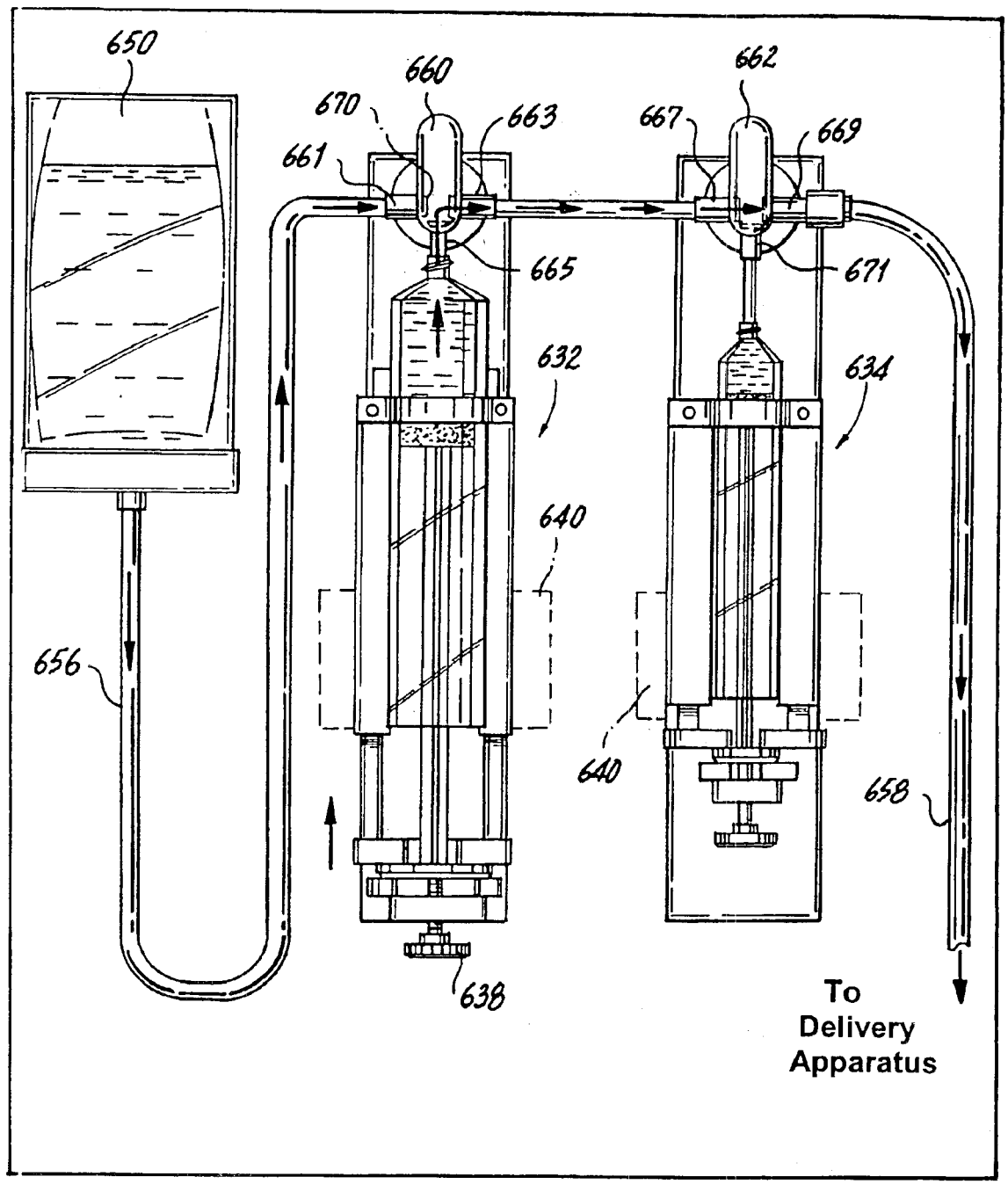
FIG. 12 is a side elevation view of the fluid pump system shown in a third position for discharging diluent from one syringe.

To discharge the prescribed volume of diluent into the vial, the process is essentially reversed with the valve 670 associated with the first leg 661 of the T connector 660 is closed to prevent flow through the first conduit 656 from the diluent source 650. The valve element associated with the second leg 669 of the second T connector 662 is opened to permit fluid flow therethrough and into the second conduit 658 to the cannula 610. The diluent that is stored in the first and second syringes 632, 634 can be delivered to the second conduit 658 in a prescribed volume according to any number of different methods, including discharging the diluent from one of the syringes 632, 634 or discharging the diluent from both of the syringes 634. For purpose of illustration only, it is described that the diluent is drawn from both of the syringes 632, 634. This arrangement is shown in FIG. 12.

The diluent contained in the first syringe 632 can be introduced into the main conduit 620 by opening the valve associated with the second leg 663 and the main body 665 of the first T connector 660 as well as opening up the valve element associated with the first leg 667 of the second T connector 662, while the valve element associated with the main body 671 of the second T connector 662 remains closed. The valve element associated with the second leg 669 remains open. The driver 640 associated with the first syringe 632 is operated to retract the plunger 638 causing a positive pressure to be exerted and resulting in a volume of the stored diluent being discharged from the first syringe 632 into the connector conduit 652 and ultimately to the second conduit 658 which is in direct fluid communication with the cannula 610. The entire volume of diluent that is needed for the reconstitution can be taken from the first syringe 632 or else a portion of the diluent is taken therefrom with an additional amount (fine tuning) to be taken from the second syringe 634.

Figure 13:
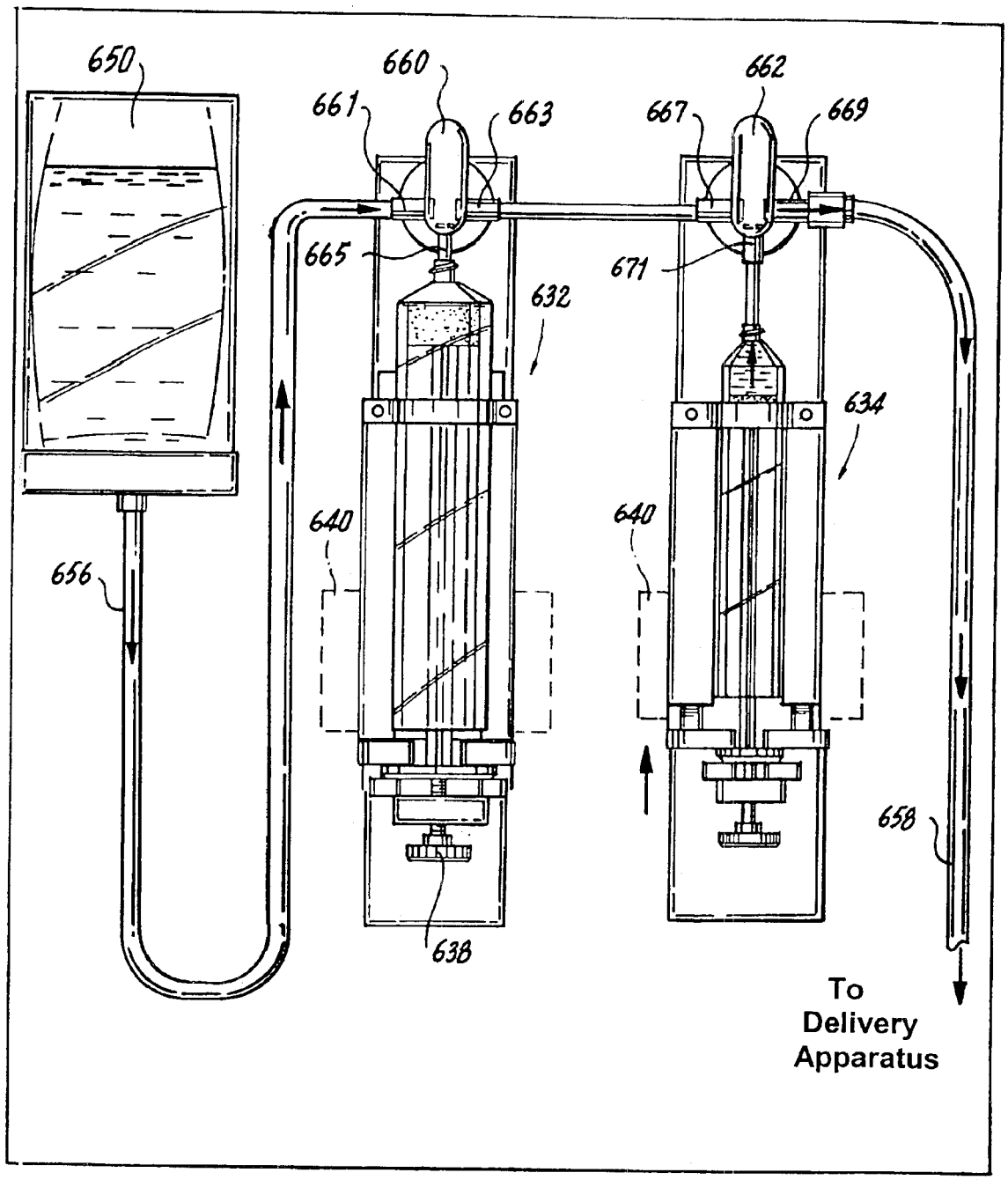
FIG. 13 is a side elevation view of the fluid pump system shown in a fourth position for discharging diluent from the other syringe.
Figure 16:
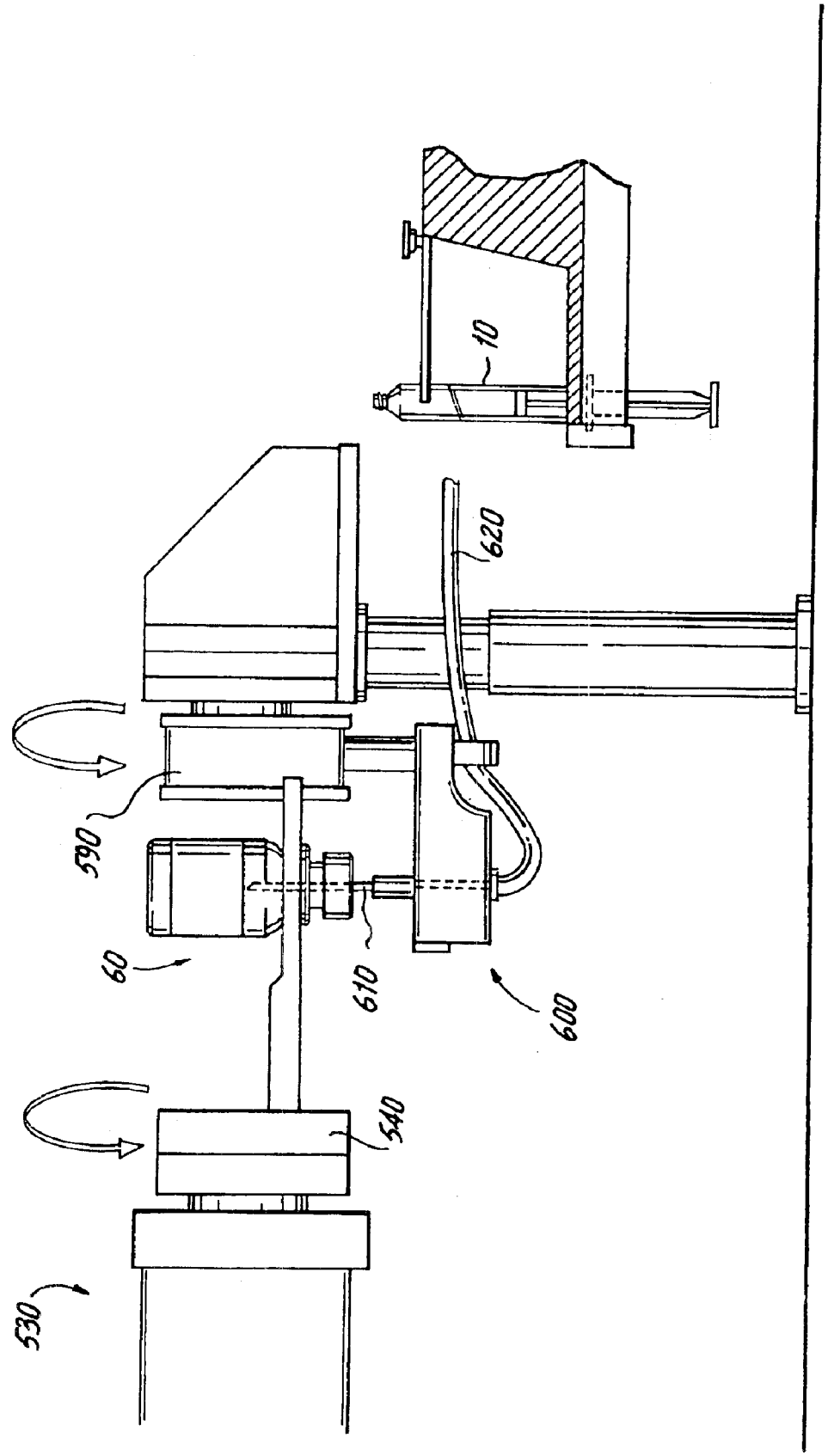
FIG. 16 is a side elevation view of the fluid transfer device in a third position in which the cannula unit and the vial gripper device are rotated to invert the cannula within the vial and to permit aspiration of the contents of the vial.
Figure 17:
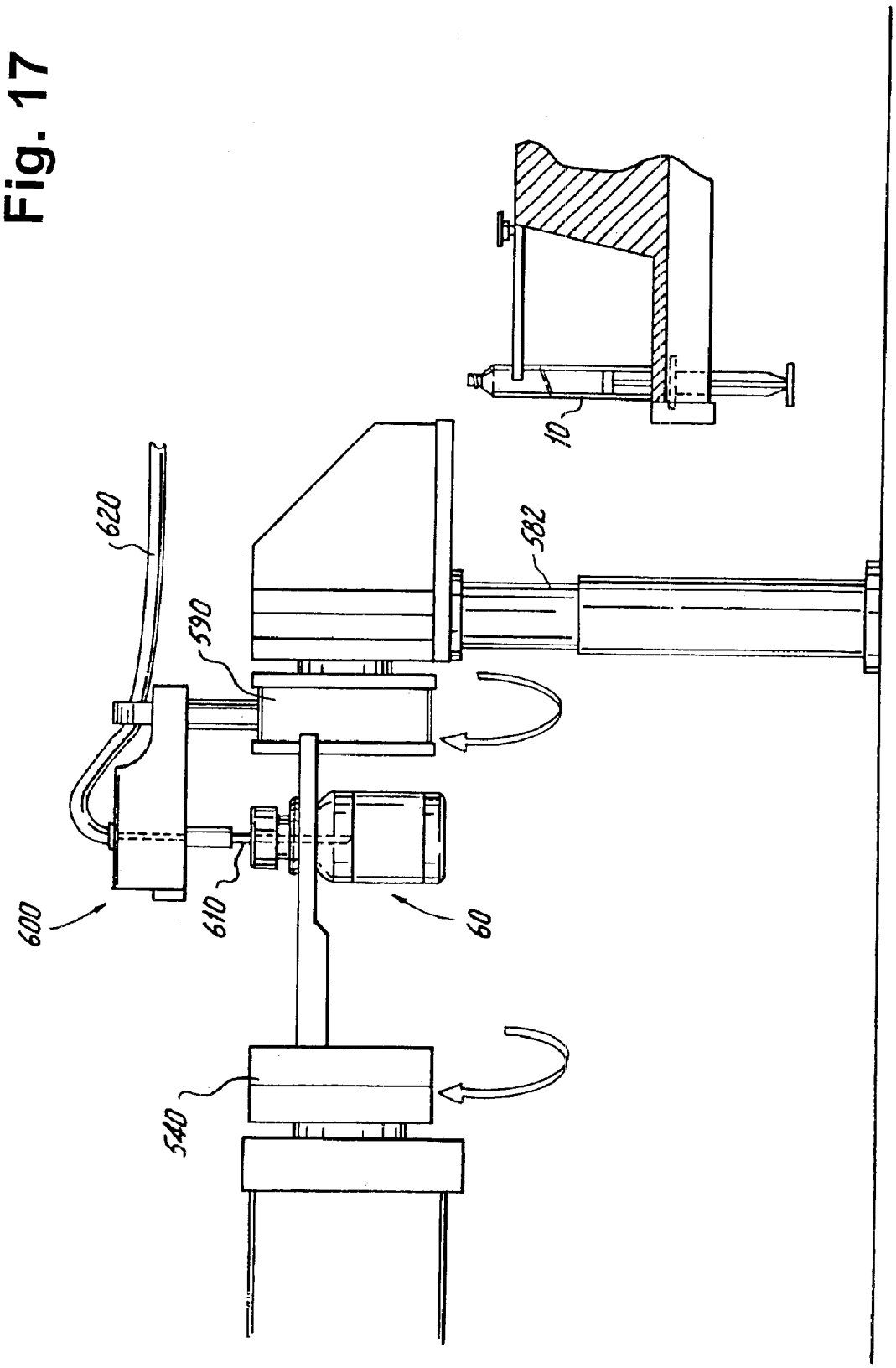
FIG. 17 is a side elevation view of the fluid transfer device in a fourth position in which the cannula unit and the vial gripper device are rotated back to the original positions.
Figure 18:
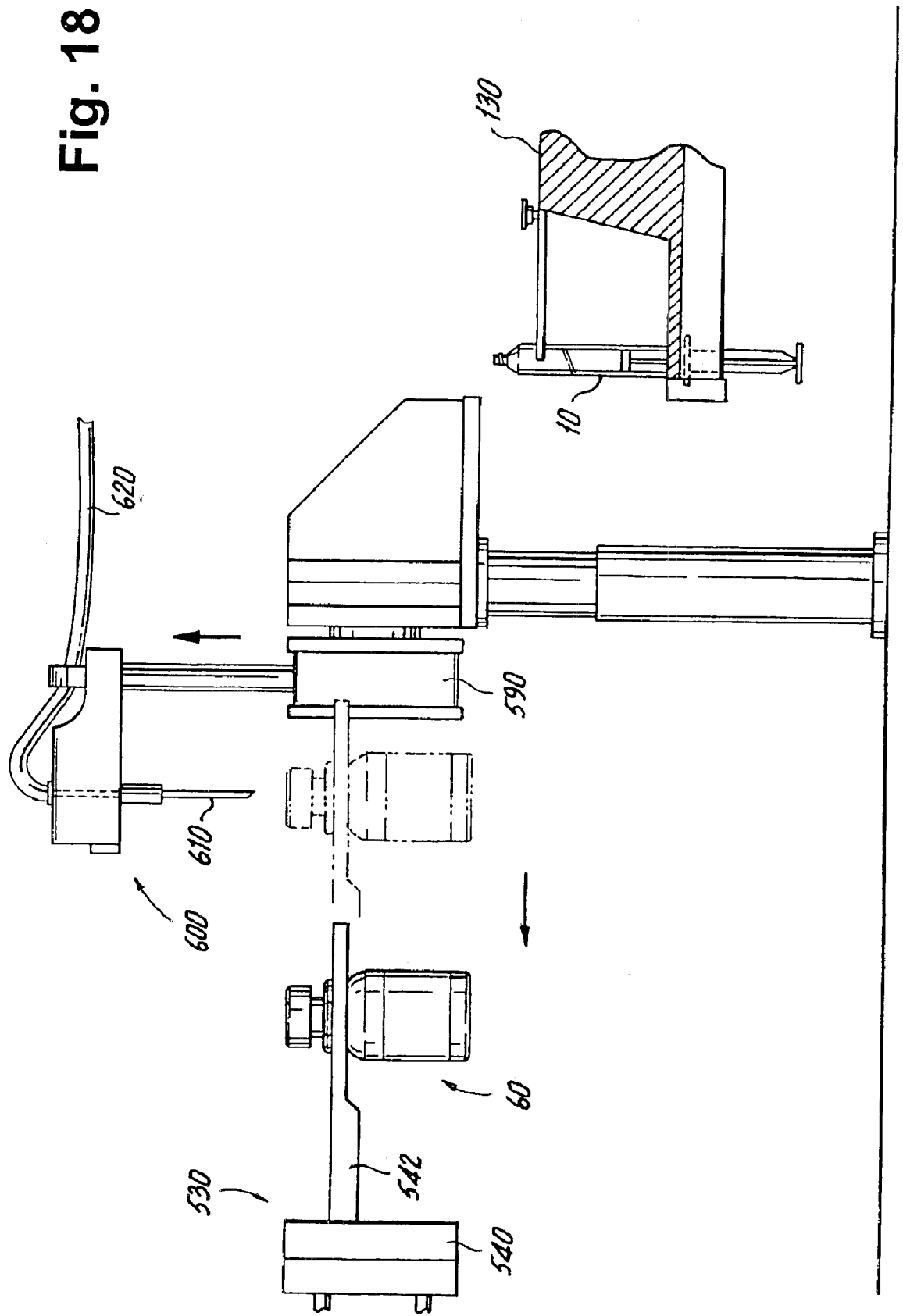
FIG. 18 is a side elevation view of the fluid transfer device in a fifth position in which the cannula unit is extended so that the cannula, with the aspirated medication, is removed from the vial.

When it is desired to withdraw diluent from the second syringe 634, the valve associated with the first leg 667 of the second T connector 662 is closed (thereby preventing fluid communication between the syringes 632, 634) and the valve associated with the main body 671 of the second T connector 662 is opened as shown in FIG. 13. The driver 640 associated with the second syringe 634 is then instructed to retract the plunger 638 causing a positive pressure to be exerted and resulting in the stored diluent being discharged from the second syringe 634 into the second conduit 658. Since the second conduit 658 and the main conduit 620 are fully primed, any new volume of diluent that is added to the second conduit 658 by one or both of the first and second syringes 632, 634 is discharged at the other end of the main conduit 620. The net result is that the prescribed amount of diluent that is needed to properly reconstitute the medication is delivered through the cannula 610 and into the vial 60. These processing steps are generally shown in FIGS. 14–16 in which the cannula 610 pierces the septum of the vial and then delivers the diluent to the vial and then the cannula unit 590 and the vial gripper device 530 are inverted to cause agitation and mixing of the contents of the vial.

It will be understood that in some applications, only one of the first and second syringes 632, 634 may be needed to operate to first receive diluent from the diluent source 650 and then discharge the diluent into the main conduit 610.

After the medication in the vial 60 has been reconstituted as by inversion of the vial and mixing, as described herein, the fluid pump system 630 is then operated so that a prescribed amount of medication is aspirated or otherwise drawn from the vial 60 through the cannula 610 and into the main conduit 620 as shown in FIGS. 16–20. Before the fluid is aspirated into the main conduit 620, an air bubble is introduced into the main conduit 620 to serve as a buffer between the diluent contained in the conduit 620 to be discharged into one vial and the aspirated medication that is to be delivered and discharged into one syringe 10. It will be appreciated that the two fluids (diluent and prepared medication) can not be allowed to mix together in the conduit 620. The air bubble serves as an air cap in the tubing of the cannula and serves as an air block used between the fluid in the line (diluent) and the pulled medication. According to one exemplary embodiment, the air block is a $\frac{1}{10}$ ml air block; however, this volume is merely exemplary and the size of the air block can be varied.

The aspiration operation is essentially the opposite of the above operation where the diluent is discharged into the vial 60. More specifically, the valve 670 associated with the first leg 661 of the first T connector 660 is closed and the valve associated with the second leg 669 of the second T connector 662 is opened to permit flow of the diluent in the main conduit into one or both of the syringes 632, 634. As previously mentioned, the second syringe 634 acts more as a means to fine tune the volume of the fluid that is either to be discharged or aspirated.

The drivers 640 associated with one or both of the first and second syringes 632, 634 are actuated for a prescribed period of time resulting in the plungers 638 thereof being extended a prescribed distance (which can be different from one another). As previously mentioned, the distance that the drivers 640 move the corresponding plungers 638 is directly tied to the volume of fluid that is to be received within the corresponding syringe 632, 634. By extending one or both of the plungers 638 by means of the drivers 640, a negative pressure is created in the main conduit 620 as fluid is drawn into one or both of the syringes 632, 634. The creation of negative pressure within the main conduit 620 and the presence of the tip end of the cannula 610 within the medication translates into the medication being drawn into the cannula 610 and ultimately into the main conduit 620 with the air block being present therein to separate the pulled medication and the fluid in the line.

It will be appreciated that the aspiration process can be conducted so that fluid is aspirated into one of the syringes 632, 634 first and then later an additional amount of fluid can be aspirated into the other syringe 632, 634 by simply controlling whether the valves in the main bodies 665, 671 are open or closed. For example, if fluid is to be aspirated solely to the first syringe 632, then the valve elements associated with the first and second legs 667, 669 of the second T connector 662 and the valve element associated with the second leg 663 and main body 665 of the first T connector 660 are all open, while the valve elements associated with the first leg 661 of the T connector 660 and the main body 671 of the T connector 662 remain closed. After a sufficient volume of fluid has been aspirated into the first syringe 632 and it is desired to aspirate more fluid into the second syringe 634, then the valve element associated with the first leg 667 simply needs to be closed and then the driver 640 of the second syringe 634 is actuated to extend the plunger 638.

Figure 19:
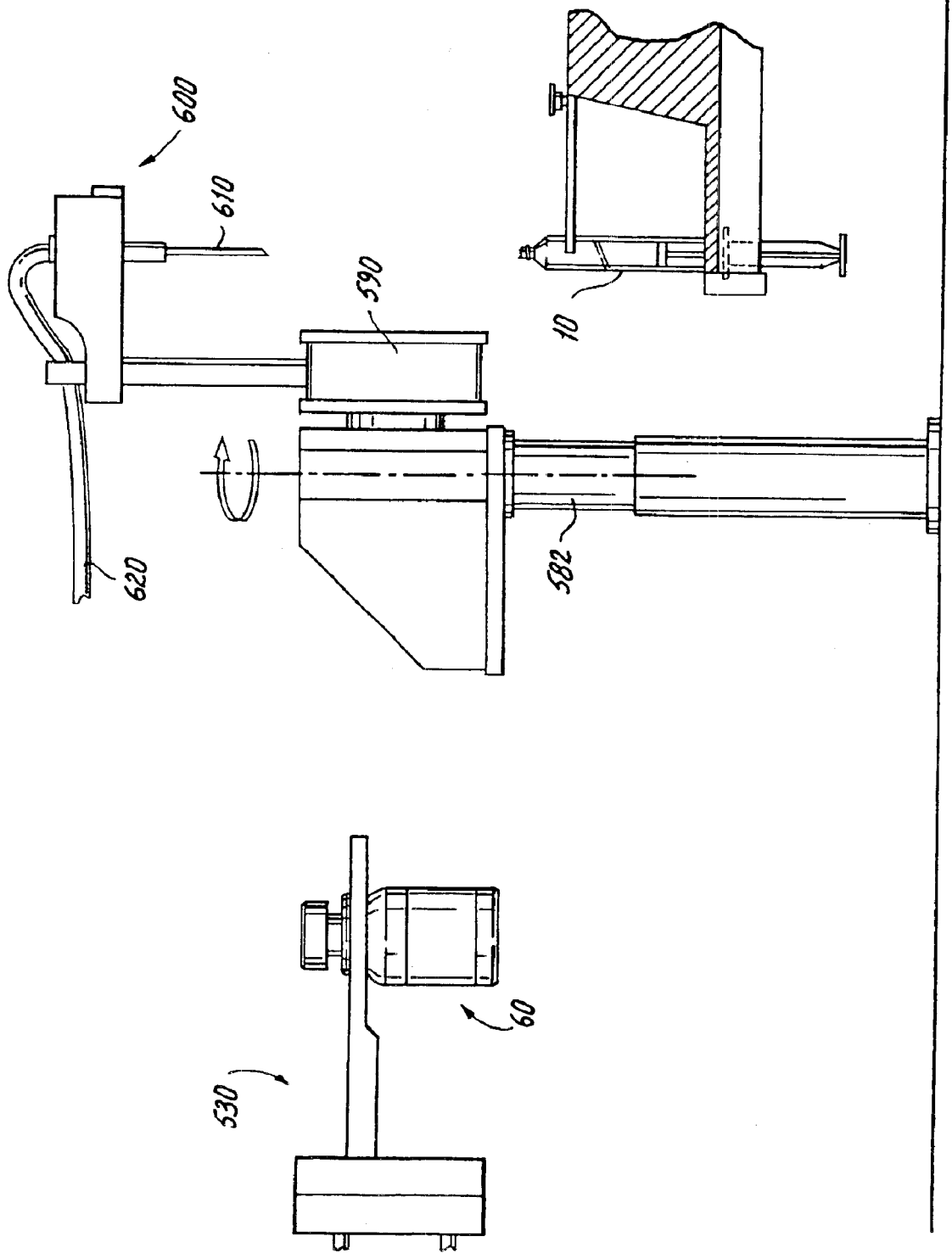
FIG. 19 is a side elevation view of the fluid transfer device in a sixth position in which the cannula unit is rotated to the rotary dial that contains the nested syringes.
Figure 20:
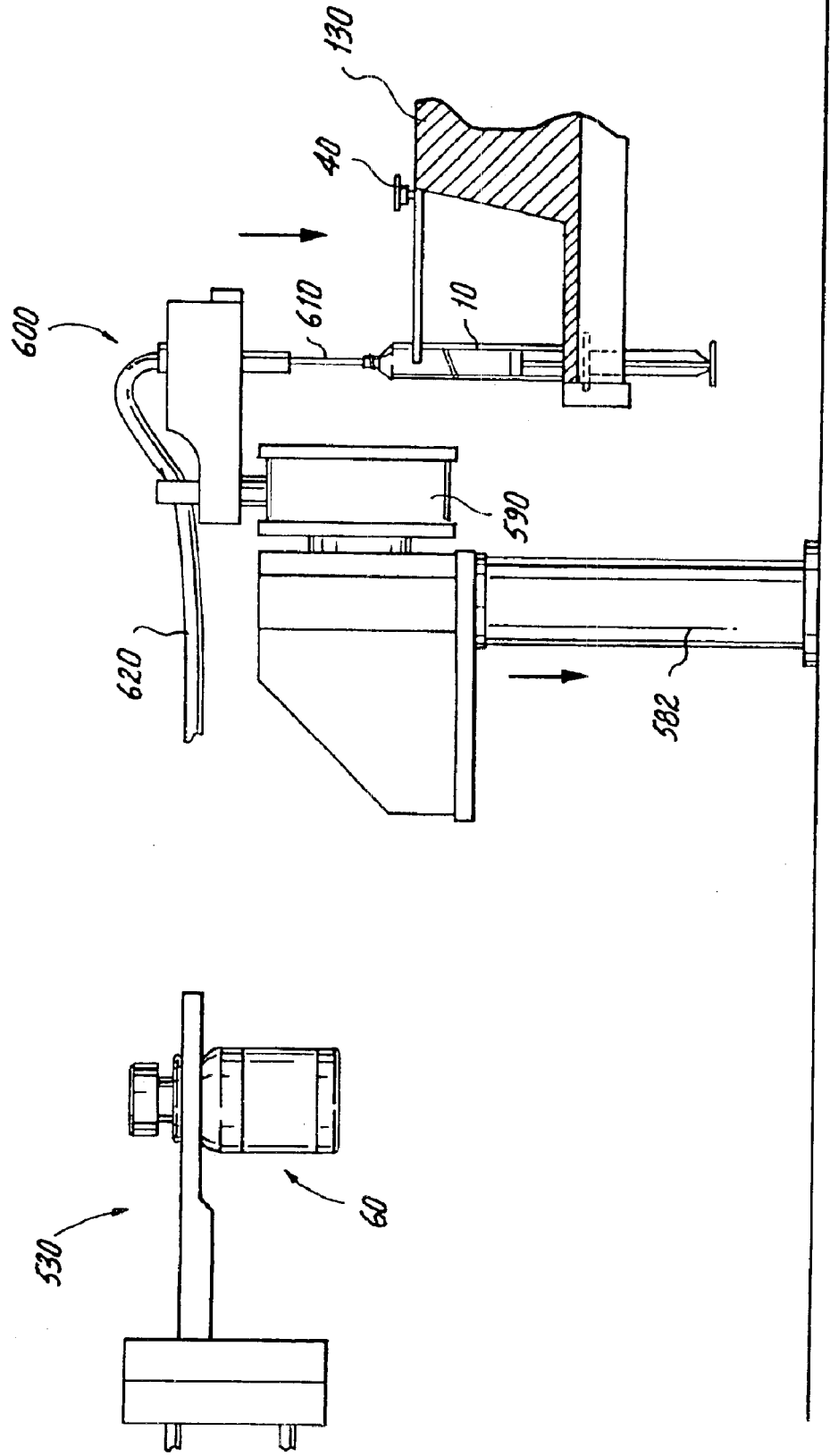
FIG. 20 is a side elevation view of the fluid transfer device in a seventh position in which the cannula unit is retracted so that the cannula thereof is inserted into the syringe to permit the aspirated fluid to be delivered to the syringe.

After aspirating the medication into the main conduit 620, the fluid transfer device 580 is rotated as is described below to position the cannula 610 relative to one syringe 10 that is nested within the rotary dial 130 as shown in FIGS. 19 and 20. Since the plungers 638 are pulled a prescribed distance that directly translates into a predetermined amount of medication being drawn into the main conduit 620, the plungers 638 are simply retracted (moved in the opposite direction) the same distance which results in a positive pressure being exerted on the fluid within the main conduit 620 and this causes the pulled medication to be discharged through the cannula 610 and into the syringe 10. During the aspiration operation and the subsequent discharge of the fluid, the valves are maintained at set positions so that the fluid can be discharged from the first and second syringes 632, 634. As the plungers 638 are retracted and the pulled medication is discharged, the air block continuously moves within the main conduit 620 toward the cannula 610. When all of the pulled (aspirated) medication is discharged, the air block is positioned at the end of the main conduit signifying that the complete pulled medication dose has been discharged; however, none of the diluent that is stored within the main conduit 620 is discharged into the syringe 10 since the fluid transfer device 580, and more particularly, the drivers 640 thereof, operates with such precision that only the prescribed medication that has been previously pulled into the main conduit 620 is discharged into the vial 60. The valve elements can be arranged so that the plungers can be retracted one at a time with only one valve element associated with the main bodies 665, 671 being open or the plungers can be operated at the same time.

It will be appreciated that the fluid transfer device 580 may need to make several aspirations and discharges of the medication into the vial 60 in order to inject the complete prescribed medication dosage into the vial 60. In other words, the cannula unit 590 can operate to first aspirate a prescribed amount of fluid into the main conduit 620 and then is operated so that it rotates over to and above one syringe 10 on the rotary dial 130, where one incremental dose amount is discharged into the vial 60. After the first incremental dose amount is completely discharged into the syringe 10, the vertical base section 582 is rotated so that the cannula unit 590 is brought back the fluid transfer position where the fluid transfer device 582 is operated so that a second incremental dose amount is aspirated into the main conduit 620 in the manner described in detail hereinbefore. The vertical base section 582 is then rotated again so that the cannula unit 590 is brought back to the rotary dial 130 above the syringe 10 that contains the first incremental dose amount of medication. The cannula 610 is then lowered so that the cannula tip is placed within the interior of the syringe 10 and the cannula unit 590 (drivers 640) is operated so that the second incremental dose amount is discharged into the syringe 10. The process is repeated until the complete medication dose is transferred into the syringe 10.

Figure 21:
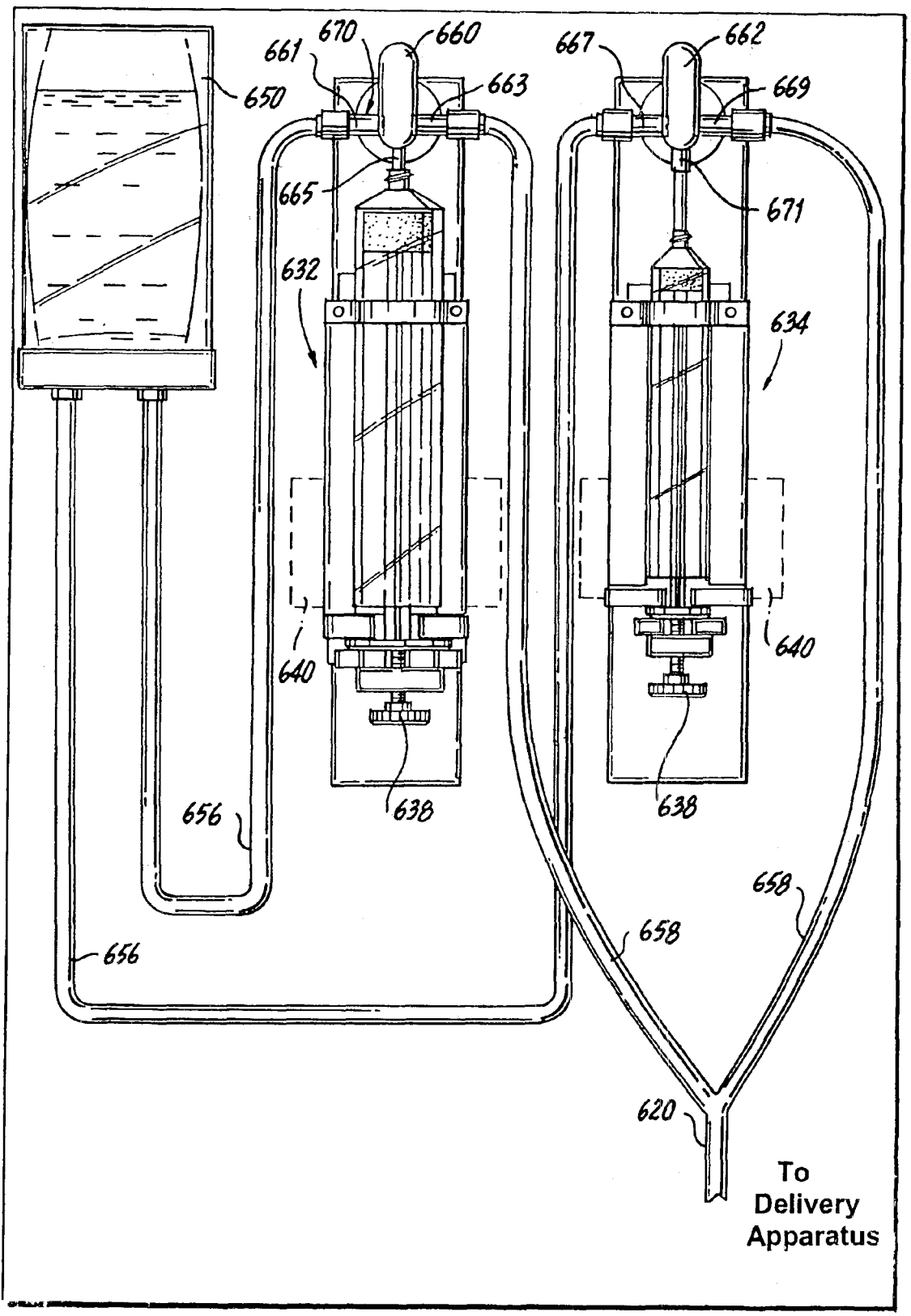
FIG. 21 is a side elevation view of a fluid pump system according to an alternate embodiment and that that is located in the fluid transfer area.

In yet another embodiment shown in FIG. 21, the two syringes 632, 634 are not directly connected to one another but instead each of the syringes 632, 634 is directly fluidly connected to the diluent source 550 and the main conduit 620. More specifically, one leg of the T connector 660 of the first syringe 632 is coupled to a first conduit 656 that is connected at its other end to the diluent source 650 and the other leg of the connector 660 is coupled to a second conduit 658 that is connected at its other end to the main conduit 620. Similarly, one leg of the T connector 662 of the second syringe 634 is coupled to a first conduit 656 that is connected at its other end to the diluent source 650 and the other leg of the connector 662 is coupled to a second conduit 658 that is connected at its other end to the main conduit 620. In this manner, when it is desired to draw diluent from the diluent source 650, the respective drivers 640 are operated to cause the respective plungers 638 to be independently extended and depending upon the distance that each is extended, a prescribed volume of diluent is drawn into the syringe. At this time, the valves 670 that are associated with the first conduits 658 are open, while those associated with the second conduits 658 are clsoed. As mentioned, the first syringe 632 typically draws a greater volume of diluent since the second syringe 634 is designed to fine tune and provide small increments of diluent to be added to the vial. Similarly, when an aspiration process is performed, the two valves associated with the first conduits 656 are closed and when the drivers 640 are operated to discharge or pump the aspirated medication, the valves 670 associated with the first conduits 656 remain closed.

Once the syringe 10 receives the complete prescribed medication dose, the vial 60 that is positioned at the fluid transfer position can either be (1) discarded or (2) it can be delivered to a holding station 700 where it is cataloged and held for additional future use. More specifically, the holding station 700 serves as a parking location where a vial that is not completely used can be used later in the preparation of a downstream syringe 10. In other words, the vials 60 that are stored at the holding station 700 are labeled as multi-use medications that can be reused. These multi-use vials 60 are fully reconstituted so that at the time of the next use, the medication is only aspirated from the vials 60 as opposed to having to first inject diluent to reconstitute the medication. The user can easily input into the database of the master controller which medications are multi-use medications and thus when the vial 60 is scanned and identified prior to being delivered to the fluid transfer position, the vial 60 is identified and marked as a multi-use medication and thus, once the entire medication dose transfer has been performed, the vial gripper device 530 is instructed to deliver the vial 60 to the holding station 700. Typically, multi-use medications are those medications that are more expensive than other medications and also are those medications that are used in larger volumes (quantities) or are stored in larger containers and therefore come in large volumes.

The holding station 700 is simply a location where the multi-use vials can be easily stored. For example, the holding station 700 is preferably a shelf or even a cabinet that contains a flat surface for placing the vials 60. Preferably, there is a means for categorizing and inventorying the vials 60 that are placed at the holding station 700. For example, a grid with distinct coordinates can be created to make it easy to determine where each vial 60 is stored within the holding station 700.

Once the device 530 has positioned the gripper unit 540 at the proper location of the holding station 700, the gripper unit 540 is operated so that the arms thereof release the vial 60 at the proper location. The device 530 then returns back to its default position where it can then next be instructed to retrieve a new vial 60 from the pedestal 520.

If the vial 60 is not a multi-use medication, then the vial 60 at the fluid transfer position is discarded. When this occurs, the device 530 moves such that the vial 60 is positioned over a waste chute or receptacle and then the gripper unit 540 is actuated to cause the vial 60 to drop therefrom into the waste chute or receptacle. The device 530 then is ready to go and retrieve a new vial 60 that is positioned at the pedestal 520 for purposes of either reconstituting the medication or simply aspirating an amount of medication therefrom or a vial from the holding station 700 can be retrieved.

As previously mentioned, during the reconstitution process, it is often necessary or preferable to mix the medication beyond the mere inversion of the vial and therefore, the vial 60 can be further agitated using a mixing device or the like 710. In one embodiment, the mixing device 710 is a vortex type mixer that has a top surface on which the vial 60 is placed and then upon actuation of the mixer, the vial 60 is vibrated or otherwise shaken to cause all of the solid medication to go into solution or cause the medication to be otherwise mixed. In yet another embodiment, the mixing device is a mechanical shaker device, such as those that are used to hold and shake paint cans. For example, the vial 60 can be placed on support surface of the shaker and then an adjustable hold down bar is manipulated so that it travels towards the vial and engages the vial at an end opposite the support surface. Once the vial 60 is securely captured between these two members, the shaker device is actuated resulting in the vial 60 being shaken to agitate the medication and ensure that all of the medication properly goes into solution. This type of mixing device can also be configured so that it is in the form of a robotic arm that holds the vial by means of gripper members (fingers) and is operatively connected to a motor or the like which serves to rapidly move the arm in a back and forth manner to cause mixing of the medication.

As briefly mentioned before, the entire system 100 is integrated and automated and also utilizes a database for storing identifying data, mixing instructions, and other information to assist in the preparation of the medication. There are also a number of safety features and check locations to make sure that the medication preparation is proceeding as it should.

For example, the database includes identifying information so that each vial 60 and syringe 10 can be carefully kept track of during each step of the process. For example, a scanner 720 and the photoimaging equipment serve to positively identify the vial 60 that is delivered from the drug storage 110. Typically, the user will enter one or more medication preparation orders where the system 100 is instructed to prepare one or more syringes that contain specific medication. Based on this entered information or on a stored medication preparation order that is retrieved from a database, the vial master controller determines at which location in the cabinet the correct vial 60 is located. That vial 60 is then removed using a robotic gripper device (not shown) and is then placed on the conveyor belt 111 and delivered to the mechanism 510 pivots upright so that the vial 60 is moved a vertical position relative to the ground and is held in an upright manner and is then delivered to the rotatable pedestal 520. At the pedestal 520, the vial 60 is scanned to attempt to positively identify the vial 60 and if the scanned identifying information matches the stored information, the vial 60 is permitted to proceed to the next station. Otherwise, the vial 60 is discarded.

Once the vial 60 is confirmed to be the right vial it proceeds to the fluid transfer position. The master controller serves to precisely calculate how the fluid transfer operation is to be performed and then monitors the fluid transfer operations has it is occurring. More specifically, the master controller first determines the steps necessary to undertake in order to perform the reconstitution operation. Most often during a reconstitution operation, the vial 60 that is retrieved from the drug storage 110 contains a certain amount of medication in the solid form. In order to properly reconstitute the medication, it is necessary to know what the desired concentration of the resulting medication is to be since this determines how much diluent is to be added to the vial 60. Thus, one piece of information that the user is initially asked to enter is the concentration of the medication that is to be delivered to the patient as well as the amount that is to be delivered. Based on the desired concentration of the medication, the master controller is able to calculate how much diluent is to be added to the solid medication in the vial 60 to fully reconstitute the medication. Moreover, the database also preferably includes instructions as to the mixing process in that the mixing device is linked to and is in communication with the master controller so that the time that the mixing device is operated is stored in the database such that once the user inputs the medication that is to be prepared and once the vial 60 is scanned and identified, the system (master controller or CPU thereof) determines the correct of time that the vial 60 is to be shaken to ensure that all of the medication goes into solution.

Once the master controller determines and instructs the working components on how the reconstitution operation should proceed, the master controller also calculates and prepares instructions on how many distinct fluid transfers are necessary to deliver the prescribed amount of medication from the vial 60 to the syringe 10. In other words, the cannula unit 590 may not be able to fully aspirate the total amount of medication from the vial 60 in one operation and therefore, the master controller determines how many transfer are needed and also the appropriate volume of each aspiration so that the sum of the aspiration amounts is equal to the amount of medication that is to be delivered to the syringe 10. Thus when multiple aspiration/discharge steps are required, the master controller instructs and controls the operation of the drivers 640 so that the precise amounts of medication are aspirated and then discharged into the syringe 10. As previously described, the syringe drivers 640 retract and advance at the right levels to cause the proper dose amount of the medication to be first aspirated from the vial and then discharged into the syringe. This process is repeated as necessary until the correct dose amount is present in the syringe 10 in accordance with the initial inputted instructions of the user.

After transferring the proper precise amount of medication to one syringe 10, the master controller instructs the rotary dial to move forward in an indexed manner so that the next empty syringe 10 is brought into the fluid transfer position. The cannula 610 is also preferably cleaned after each medication dose transfer is completed so as to permit the cannula 610 to be reused. There are a number of different techniques that can be used to clean the cannula 610 between each medication transfer operation. For example, the cleaning equipment and techniques described in commonly assigned U.S. Pat. No. 6,616,771 and U.S. patent application Ser. No. 10/457,898 (both of which are hereby incorporated by reference in their entireties) are both suitable for use in the cleaning of the cannula 610.

In one embodiment, the cannula 610 is rotated and positioned so that the needle of the cannula 610 is lowered into a bath so that fluid is expelled between the inside hubs of the syringe 10 for cleaning of the interior components of the cannula 610. The cannula 610 is then preferably dipped into a bath or reservoir to clean the outside of the cannula 610. In this manner, the cannula 610 can be fully cleaned and ready for a next use without the need for replacement of the cannula 610, which can be quite a costly endeavor.

Figure 22:
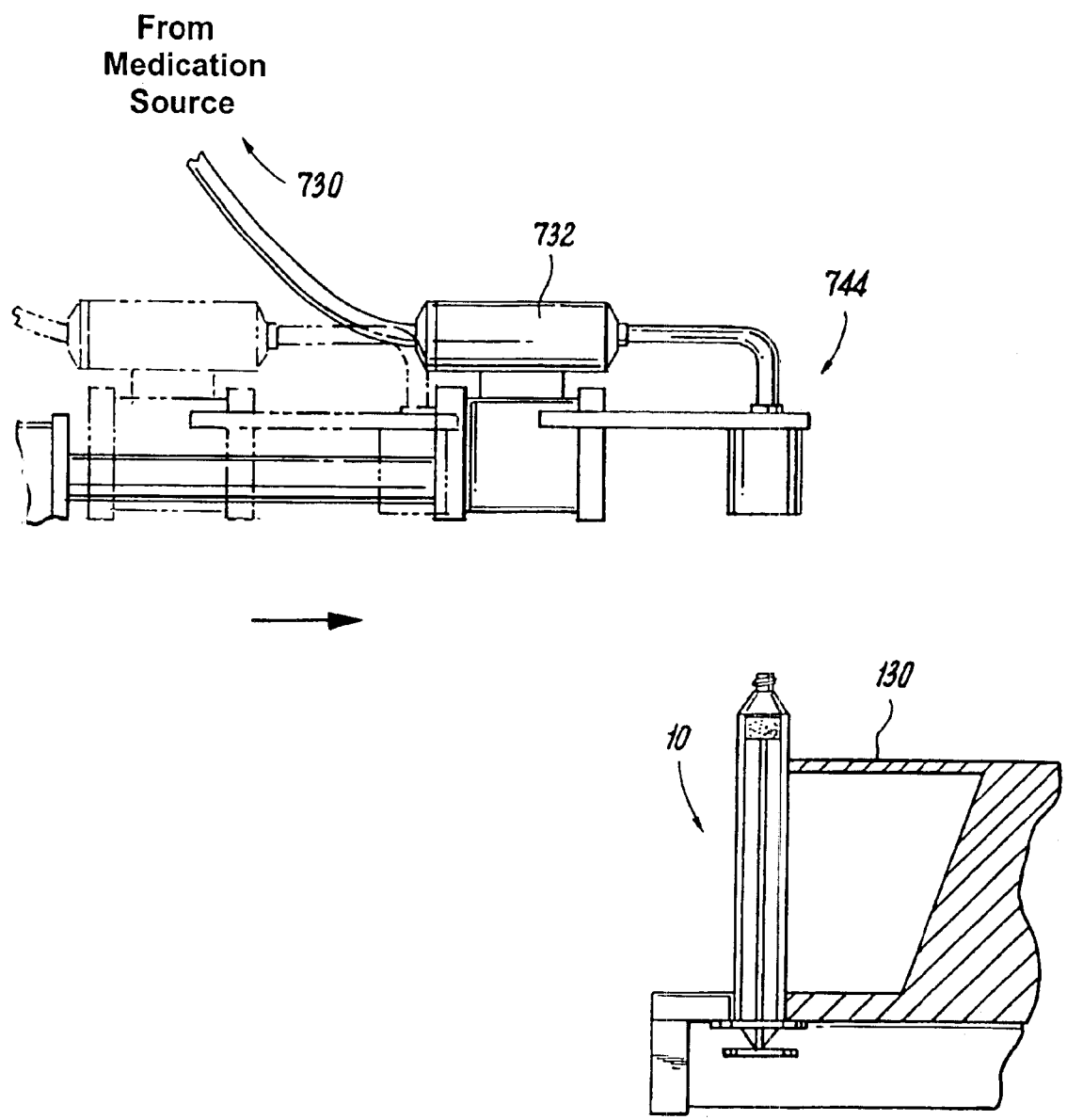
FIG. 22 is a side elevation view of an alternative arrangement where stored medication is delivered through a conduit to a connector apparatus for sealingly mating with an open tip cap of the syringe and wherein extension of the syringe plunger causes a prescribed dose amount of medication to be drawn into the syringe barrel.
Figures 23, 24:
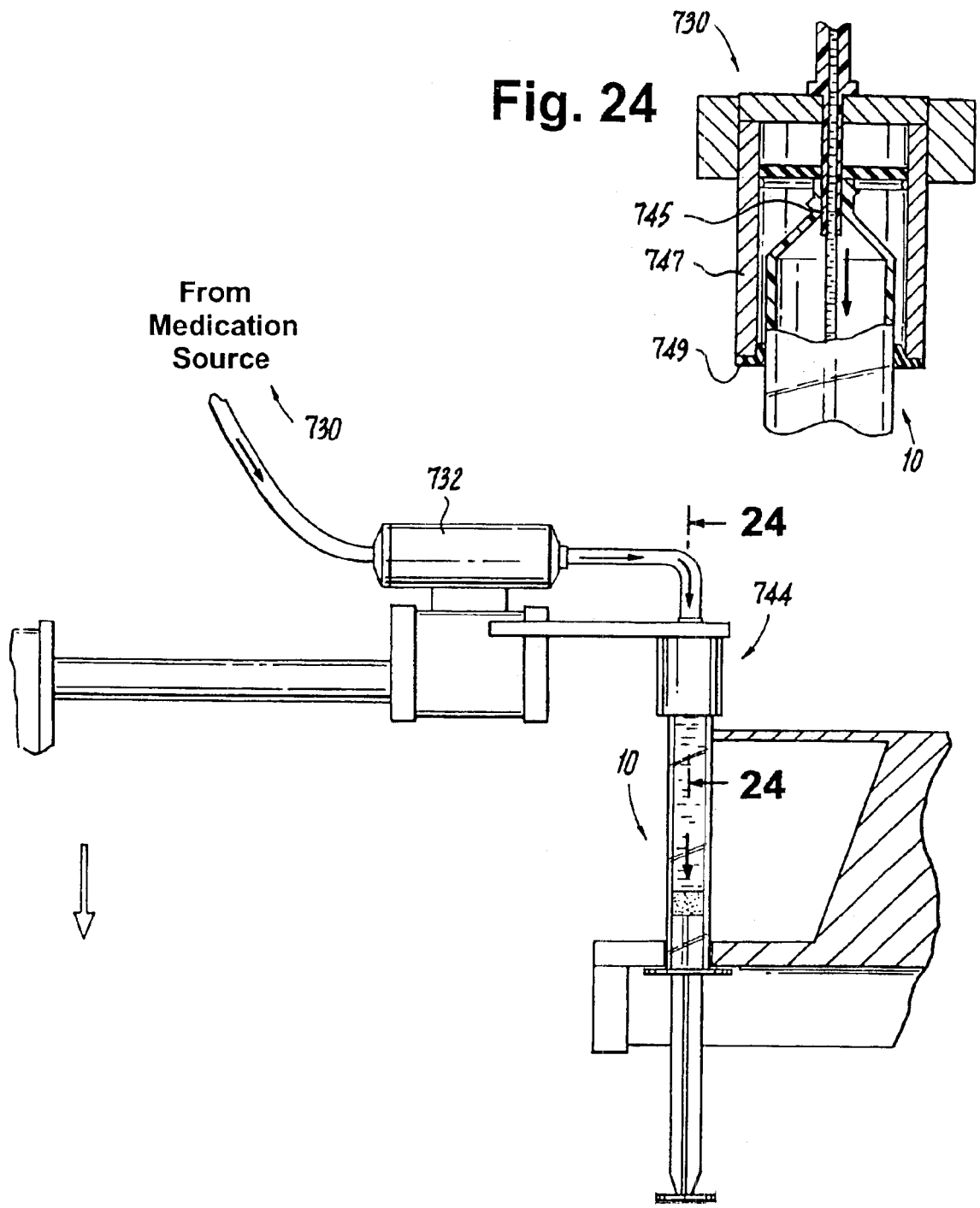
FIG. 23 is a side elevation view of the connector apparatus sealed with the syringe and the plunger being extended.
FIG. 24 is a local perspective view showing the mating between the connector and the syringe.

In yet another embodiment illustrated in FIGS. 22–24, a medication source 730, such as a bag that is filled with liquid medication that has already been properly reconstituted, is connected to an input portion of a peristaltic pump 732 by means of a first conduit section 740. A second conduit section 742 is connected to an output port of the pump 732 and terminates in a connector 744. The connector 744 is of the type that is configured to hermetically seal with an open barrel tip of the syringe 10 that is nested within the rotary dial 130 and is marked to receive medication. The connector 744 typically includes a conduit member 745 (tubing) that is surrounded by a skirt member or the like 747 that mates with the outer hub of the syringe barrel. A flange or diaphragm 749 can be provided as shown in FIG. 24 for hermetically sealing with the syringe barrel (outer hub).

In commonly assigned U.S. patent application Ser. No. 10/457,066 (which is hereby incorporated by reference in its entirety), it is described how the plunger 50 of the syringe 10 can be extended with precision to a prescribed distance. In that application, the plunger 50 is extended to create a precise volume in the barrel that is to receive the medication that is injected therein at a downstream location. However, it will be appreciated that the action of extending the plunger 50 can serve more than this purpose since the extension of the plunger 50 creates negative pressure within the syringe barrel and thus can serve to draw a fluid therein. For example, once the connector 744 is sealingly mated with the open syringe tip end, the medication source 730 is fluidly connected to the syringe 10 and thus can be drawn into the syringe barrel by means of the extension of the plunger 50. In other words, the plunger 50 is pulled a precise distance that results in the correct size cavity being opened up in the barrel for receiving the fluid but also the extension of the plunger creates enough negative pressure to cause the medication to be drawn into the syringe barrel. This is thus an alternative means for withdrawing the proper amount of medication from a member (in this case the source 730) and transferring the desired, precise amount of medication to the syringe 10. The operation of this alternative embodiment can be referred to as operating the system in reservoir mode. One advantage of this embodiment is that multiple syringe drivers are not needed to pump the medication into the syringe 10 but rather the drawing action is created right at the rotary dial 130. This design is thus fairly simple; however, it is not suitable for instances where drug reconstitution is necessary.

Prior to its using another drug, the cannula 610 is cleaned using conventional techniques, such as those described in the previously incorporated patents and patent applications.

After the medication is aspirated into the barrel 20, the dial 130 is advanced so that the filled syringe 10 is delivered to the sixth station 180 (FIG. 2). For example, the dial 130 is preferably advanced so that the filled syringe 10 is delivered to a station where the removed tip cap 40 is replaced back onto the barrel tip 28 by a device 900. Referring to FIGS. 25 and 26, the device 900 can be similar or identical to the device 300 that removes the tip cap 40 from the barrel tip 28 at an earlier station or the device 900 can be different from the device 300 so long as the device 900 is configured to grasp the tip cap 40 from the post 161 and then place the tip cap 40 back on the barrel tip 28.

For purpose of illustration and simplicity, the device 900 will be described as being of the same type as device 300. The automated device 900 is a robotic device and preferably, the automated device 900 is a linear actuator with a gripper. The device 900 has a vertical base 910 which is adjustable in at least several directions. For example, the vertical base 910 has an independent reach (y axis) and vertical axis (x axis) which provides part of the flexibility and motion control that is desirable for the device 900. The vertical base 910 has an upper end 912 and an opposing lower end 914 which is operatively coupled to other movable components to permit the vertical base 910 to move in an up/down direction along the x axis and in lateral directions along the y axis. The upper end 912 is connected to a horizontal support member 920 that extends outwardly away from the vertical base 910. In one exemplary embodiment, the lower end 614 is disposed between two support beams that are part of a robotic device and are moved in a number of different directions, including along the x axis and the y axis.

A block member 930 is connected to the horizontal support member 920 and more specifically, the block member 930 is disposed on an underside of the horizontal support member 920 so that it is spaced away from the vertical base 910. The exemplary block member 930 has a block-like shape and is connected to the underside of the horizontal support member 920 by one or more connectors that can be in the form of support columns, etc.

The device 900 has first and second positionable gripping arms 940 which are adjustable in at least one direction and which are coupled to and extend downwardly from the block member 930. For example, each of the gripping arms 940 is movable at least in a direction along the y axis which provides the flexibility and motion control that is desirable in the present system 100. The gripping arms 940 are programmed to work together in tandem so that both arms 940 are driven to the same location and the same time.

The block member 930 can house some of the electronic or hydraulic components and the like that permit the gripping arms 940 to move between the open and closed positions. The coupling between the block member 930 and the gripping arms 940 is such that the gripping arms 940 have the necessary degree of movement to permit the opening and closing thereof.

Each of the gripping arms 940 is a generally L-shaped member that is formed of a vertical section 942 and a horizontal gripping section (not shown) that extends outwardly from one end of the vertical section 942. The gripping section has a cut-out or notch 360 (FIG. 3) formed therein for receiving and gripping a section of the barrel 20 of the syringe 10. Accordingly, the notch has a complementary shape as the shape of the barrel 20. One exemplary notch has a generally semi-circular shape and it seats against approximately ½ of the outer circumferential surface of the syringe barrel 20. By being movable along at least the y axis, the gripping arms 940 can be positioned between an open position in which the opposing gripping sections of the arms 940 are spaced apart from one another a sufficient distance to permit the tip cap 40 to be received therebetween.

In the closed position, the gripping sections of the arms 940 are brought together so that they either seat against one another or are in very close proximity to one another. When the gripping sections come together in the closed position, the notches define a complete circular opening that has a diameter about equal to or slightly less than the diameter of the base section 41 of the tip cap 40, thereby permitting the tip cap 40 to nest within the gripping sections 944.

In a first open position of the gripping arms 940, the gripping sections being spaced sufficiently from one another so as to permit the tip cap 40 to be freely disposed between the gripping sections. Using a control unit 950 (e.g., a programmable actuator, microprocessor, etc.), the gripping arms 940 are driven to the first position shown in FIG. 14. The control unit 950 instructs the device 900 to perform an operation where the tip cap 40 resting on the post 161 is gripped and removed by the device 900. When such an operation is performed, the vertical base 910 is driven inwardly toward the dial 130 and upwardly so that the gripping arms 940 are positioned over the tip cap 40 that is disposed on top of the post 161. The vertical base 910 is then driven downward until the gripping arms 940 are disposed around the tip cap 40. In other words, the tip cap 40 is disposed between the gripping section of the opposing arms 940 and more specifically, the gripping sections 944 are disposed adjacent the base section 41 of the tip cap 40 underneath the flange 43 with the notches being aligned with the outer surface of the base section 41. An actuator or the like of the device 900 is then activated causing the gripping arms 940 to move inwardly toward one another until the gripping sections 944 seat against the outer surface of the base section 41 of the tip cap 40. Preferably, a hydraulic or pneumatic system can be used to move the gripping arms 940 between their relative positions. In this closed position, the gripping arms 940 apply a force against the base section 41 so that the tip cap 40 is securely held by the gripping sections. When the gripping arms 940 are driven to the closed position, the gripping sections may seat against one another and the notches align such that the gripping sections substantially encircle the base section 41.

After the tip cap 40 is nested within the gripping sections, the control unit 950 directs the vertical base 910 upward and this motion causes the tip cap 40 to be removed from the post 161. After the tip cap 40 is freed from the post 161, it remains held between the gripping sections of the opposing arms 940. The vertical base 910 is then driven in a direction away from the dial 130 until the held tip cap 40 is positioned over the barrel tip 28. Once the tip cap 40 is disposed over the barrel tip 28 of the filled syringe 10, the controller 950 instructs the vertical base 910 to move downwardly so that the tip cap 40 is placed on the barrel tip 28 as shown in FIG. 15. The actuator is then activated causing the gripping arms 940 to move to the open position, thereby releasing the tip cap 40. The tip cap 40 is now firmly secured back on the barrel tip 28. The device 900 then is returned to its initial position, the dial 130 is advanced and the operation is repeated with the device 900 gripping and replacing one tip cap 40 back on the next uncapped syringe 10 that is advanced to this station.

The capped syringe 10 can then be transferred to other stations, such as a station where the syringe in bandolier form is cut into individual syringes 10 that are labeled for particular patients. The syringes 10 can then be unloaded from the dial 130 by manipulating the second retaining member 136 and more specifically, the operable pivotable arms 143, 145, (FIG. 3) are opened after an unloading gripper (not shown) grips the barrel 20 of the syringe 10 and withdraws it from the dial 130. The syringe 10 is then further processed as for example by being delivered to a storage receptacle where it is stored or by being delivered to a transporting device for delivery to the patient.

Preferably, the automated system includes at least one additional station, namely station 197 at which the tip cap 40 is made tamper proof or more precisely it is made tamper evident. More specifically, station 197 is designed as a station where an operation is performed on the tip cap 40 so that the tip cap 40 is made tamper evident by adding a tamper evident feature to the tip cap 40 that permits a consumer or user to easily determine whether the tip cap 40 has been tampered with and therefore warranting the discarding of the syringe 10. There are a number of different types of tamper evident operations that can be performed at station 197 so long as the result is that the tip cap 40 is made tamper evident. The operations discussed below are merely exemplary and illustrative and in no way limit the present invention in terms of which types of tamper evident operations can be performed.

Figure 28:
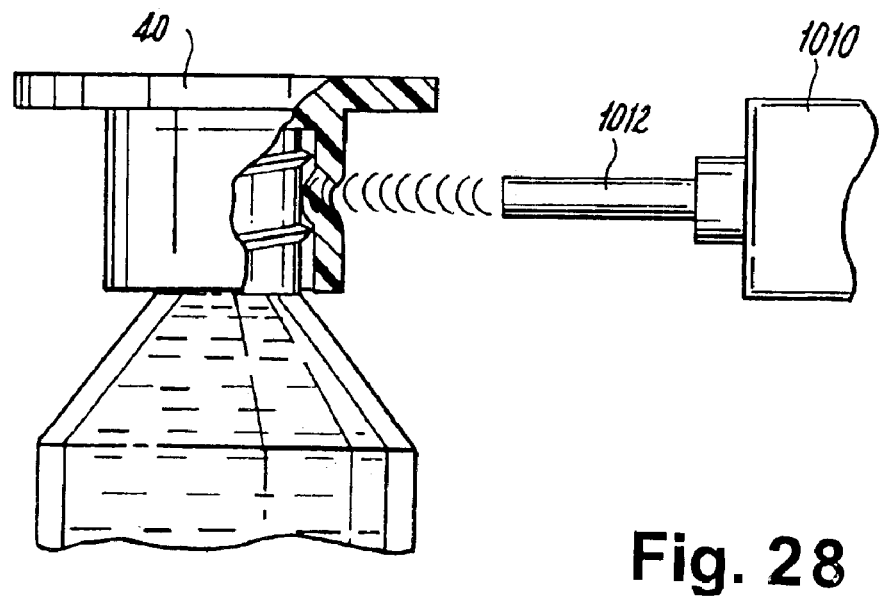
FIG. 28 is a local elevation cut-away showing a local weld produced using the device of FIG. 27.
Figure 29:
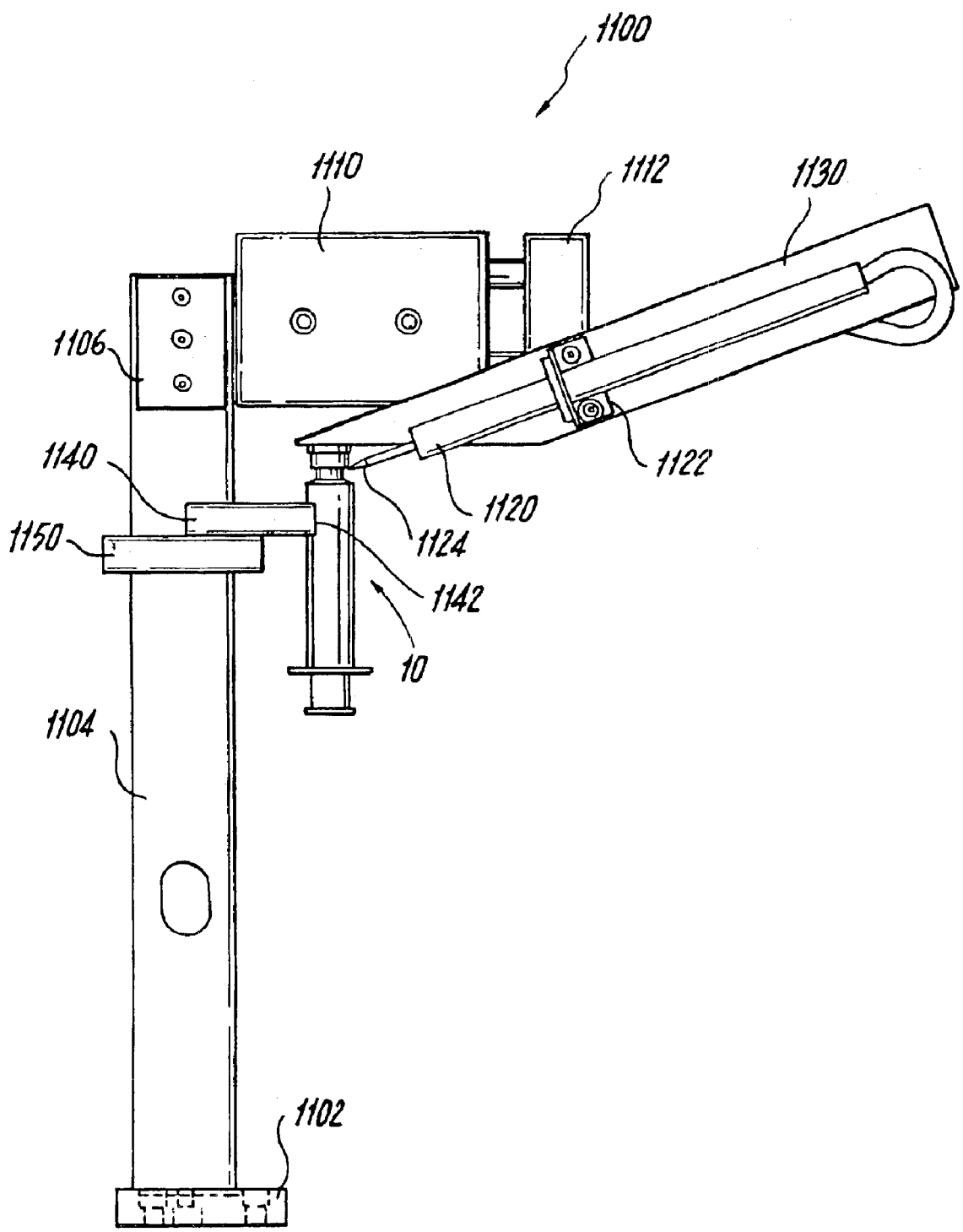
FIG. 29 is side elevational view of a heat staking welding station assembly with a welding tip according to a first embodiment.
Figure 30:
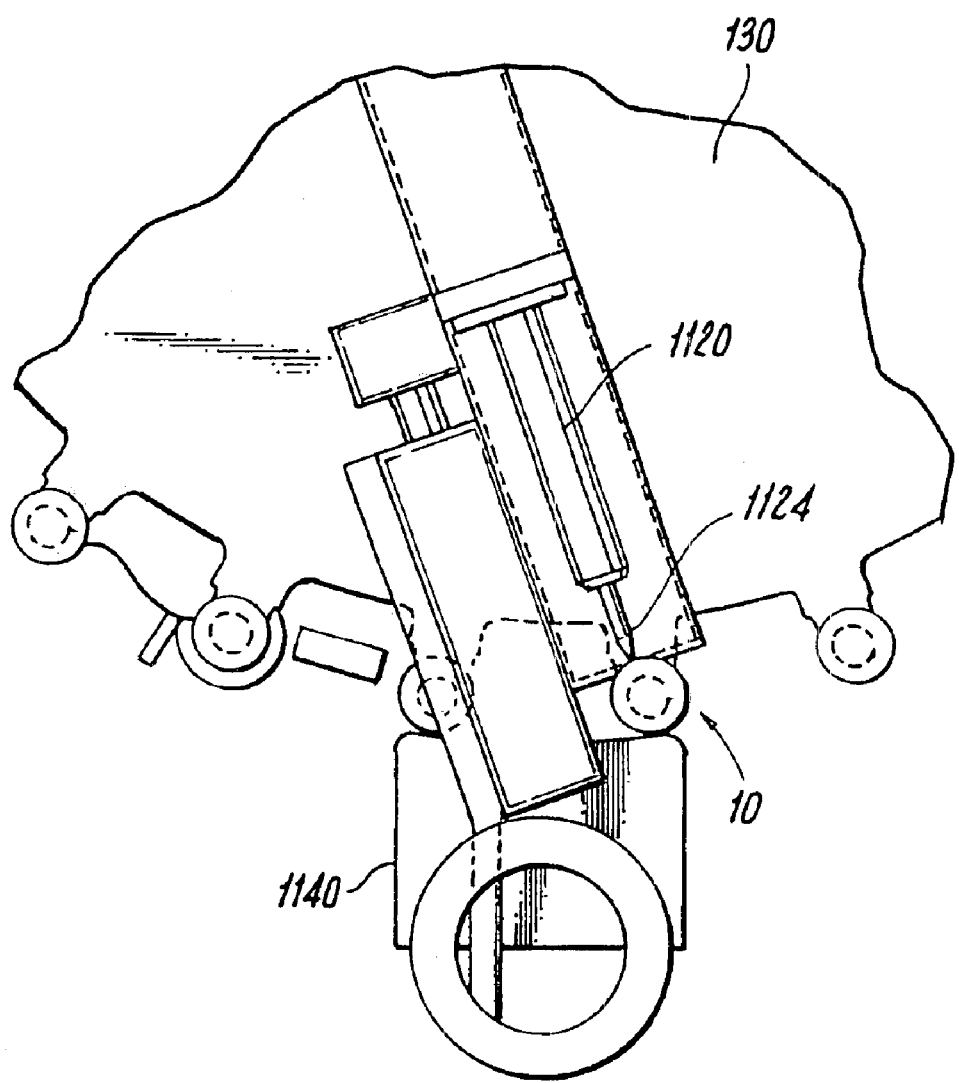
FIG. 30 is a top plan view of the heat staking welding station assembly with a rotary device holding a number of syringes.
Figure 31:
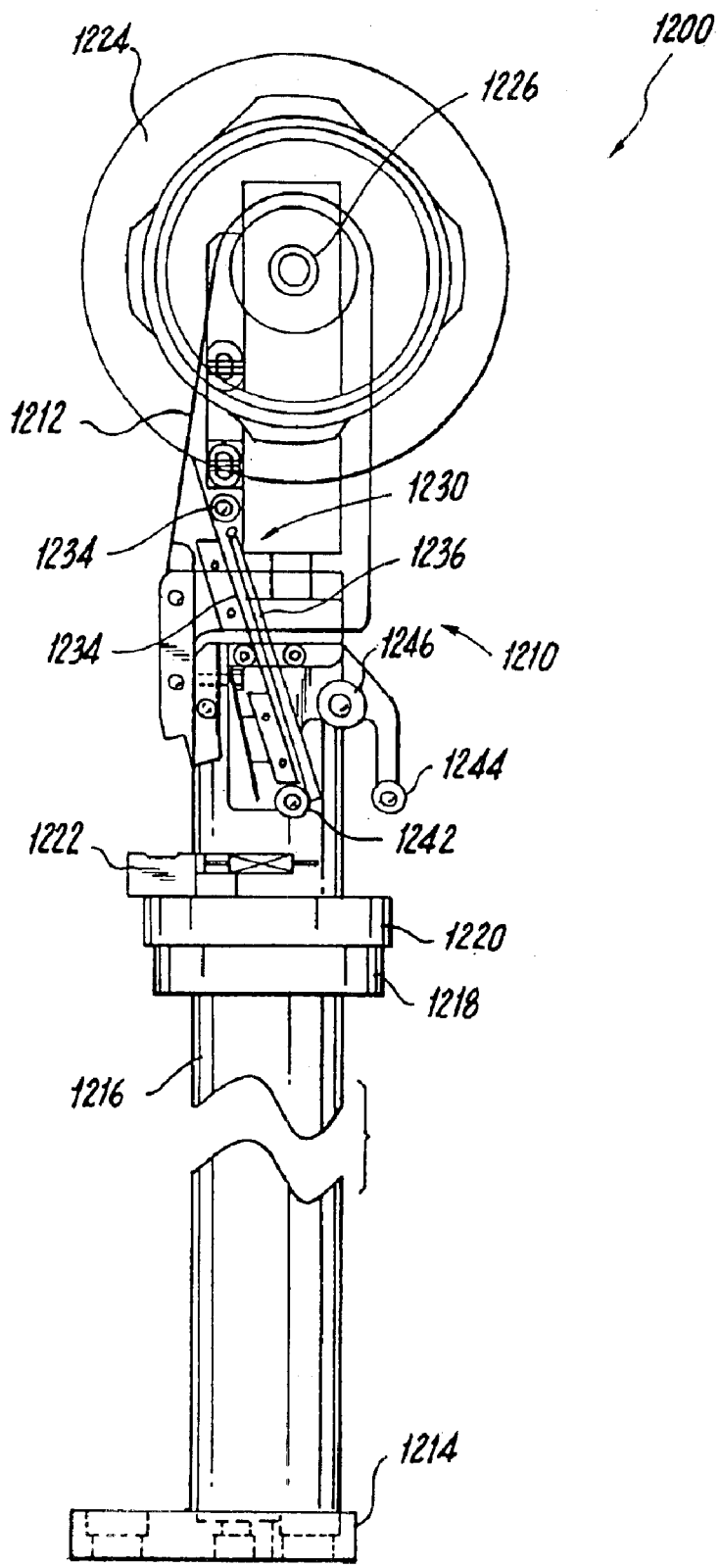
FIG. 31 is a side elevation view of an exemplary tamper evident tape sealing station.
Figure 32:
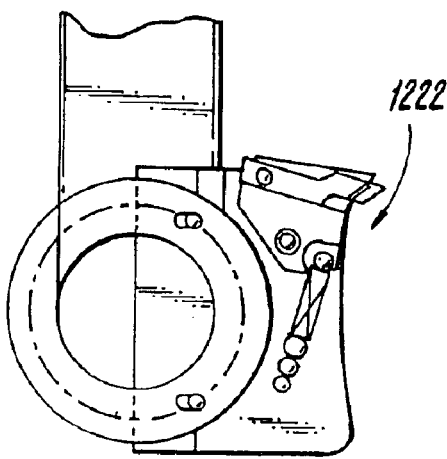
FIG. 32 is a top plan view of a section of the tape sealing station of FIG. 31.

In one exemplary embodiment and as illustrated in FIGS. 2 and 29–30, station 197 is a heat-staking station where a device is provided to perform a heat-staking operation on the tip cap 40. Heat-staking makes use of direct contact-heated tools and precisely controlled time, temperature, pressure and cooling to reform plastic studs, walls and protrusions. The heat-staking device includes a tool that is used to produce the heat-stake (local weld) between the flange of the tip cap 40 and the underlying portion of the syringe 10, namely the barrel tip 28 (outer hub of the leur assembly). The heat-stake between the tip cap 40 and the outer hub is in the form of a localized area where the two plastic parts are joined together (e.g., a small localized welded spot) (e.g., see FIG. 28). As mentioned, the time, temperature, pressure and cooling steps of the heat-staking operation are closely monitored and controlled so that the desired result is obtained as opposed to a situation where a localized welded spot is not formed between the two parts. For example, if the temperature of the heat-staking operation is not hot enough, the heat from the tool will not penetrate deep enough through the tip cap 40 and into the barrel tip (outer hub) and this results in no spot weld being formed between the two plastic parts. Conversely, if the temperature is too hot, the heat from the tool will penetrate the barrel tip (outer hub) resulting in a hole or other imperfection being formed in the barrel tip and this can lead to contamination or otherwise results in the syringe 10 being unfit for use. Thus, it is important that the position, temperature, etc. of the tool be controlled to ensure that the desired small heat-stake be formed between the two plastic parts.

The tool can be in the form of a heated probe, hot nail, solder iron tip, etc., so long as it is designed as a tool that is intended for use in a heat-staking process to produce a heat-stake between the two plastic parts. Preferably, the syringe 10 is held tightly in place when the heat-staking operation is performed so that when the tool makes contact with the outer surface of the tip cap 40, the syringe 10 does not move. For example, an automated gripper can be driven into place to grasp and hold the syringe 10 in place, while the tool is then moved into place and into contact with the outer surface of the tip cap 40. The gripper can thus include gripper fingers or otherwise have a contoured slot that receives the syringe 10 such that the movement of the syringe 10 is restricted.

The heat-stake serves to make the tip cap 40 tamper evident since the user will feel noticeable resistance and notice a pronounced "snap" when the tip cap 40 is twisted from the syringe when the user is attempting to remove the tip cap 40 prior to using the syringe 10. This "snap" signals that the syringe 10 is intact and has not been tampered with, or inadvertently has been after the cap has been removed and replaced after the syringe 10 was prepared. It will be appreciated that the user needs to twist the tip cap 40 to a sufficient degree to overcome the strength of the bond between the tip cap 40 and the syringe barrel in order to open the syringe 10 and break the bond which is evidenced by the "snap" noise.

FIGS. 29 and 30 illustrate in detail an exemplary heat staking assembly 1100 that includes a controllable welding tip 1110 that performs the heat staking operation. The assembly includes a base mount 1102 that can be affixed to a support surface, such as a floor, and a vertical standoff 1104 that extends upwardly therefrom. A second end 1106 of the standoff 1104 is coupled to a actuator 1110 which extends outwardly therefrom. At one end of the actuator 1110 there is a mount 1112 that is driveable in that it can be extended and retracted relative to a base portion of the actuator 1110. One exemplary actuator 1110 is in the form of a pneumatic cylinder. At a distal end of the mount 1112, a heat stake device 1120 is mounted thereto using conventional techniques, such as using one or more fasteners. A mounting plate 1122 or the like can be used to mount the device 1120 to the mount 1112.

The heat staking device 1120 is an elongated member that has a tip end 1124 that is heated and is used to produce the heat stake (e.g., spot weld) or the like that is in the form previously mentioned. The device 1120 can be in the form of any number of conventional heat staking devices. Preferably, the device 1120 is pivotally mounted to the mount 1112 so that the device 1120 can be adjusted in at least an up-down manner. In addition, a protective cover 1130 is preferably used to cover the device 1120 so that an individual is shielded from the actual heat staking operation that is performed at the tip end 1124. In other words, one end of the protective cover 1130 extends beyond the tip end 1124 so that it can cover a syringe 10 that is placed into a position so that the heat staking operation can be performed. The protective cover 1130 can be mounted to the mounting plate 1122.

Along a length of the vertical standoff 1104, a syringe holder 1140 is provided for holding in place at least one syringe 10. The syringe holder 1140 is in the form of a substrate that is movable relative to the standoff 1104. The syringe holder 1140 can be provided above a collar 1150 that is formed around the standoff 1104. As shown in FIG. 30, the holder 1140 is a plate-like member that has a slightly curved surface 1142 that seats against the barrel of the syringe 10 as the syringe 10 is moved into position for the heat staking operation to be performed. For example, the syringe 10 can be securely held by the rotary dial 130 that rotates in an indexed manner and as described below, when the syringe 10 is moved into the heat staking station 1100, the holder 1140 is extended so that the surface 1142 seats against the barrel of the syringe with the syringe being securely held in position between the holder 1140 and the rotary dial 130.

Once the syringe is held in place, the heat staking assembly is actuated to cause the heat stake device 1120 to be drawn in towards the syringe 10 so as to position the tip end 1124 in close proximate relation to the tip cap 40 of the syringe. The device 1120 is drawn in towards the syringe 10 by retracting the mount 1112 within the cylinder that forms a part of the actuator 1110. The working components of the assembly are preferably all in communication with a master controller that controls the movements of the working components and therefore, when the assembly is actuated when a new syringe 10 is indexed forward into a heat staking operation position, the actuator 1110 is operated to drive the heat stake device 1120 into position such that the tip end 1124 is brought into contact with the tip cap of the syringe 10 for a predetermined period of time and at a predetermined pressure to form a welded heat stake of the type mentioned hereinbefore. After the predetermined period of time has lapsed, the actuator 1110 is operated to cause the mount 1112 to extend, thereby driving the tip end 1124 away from contact with the tip cap of the syringe. The process then continues by moving the rotary device 1130 in an indexed manner so that the completed heat staked syringe is removed from the station 1100 and another syringe 10 is advanced into the station 1100. In this embodiment, the station 1100 is one where a welding operation is performed.

Figure 27:
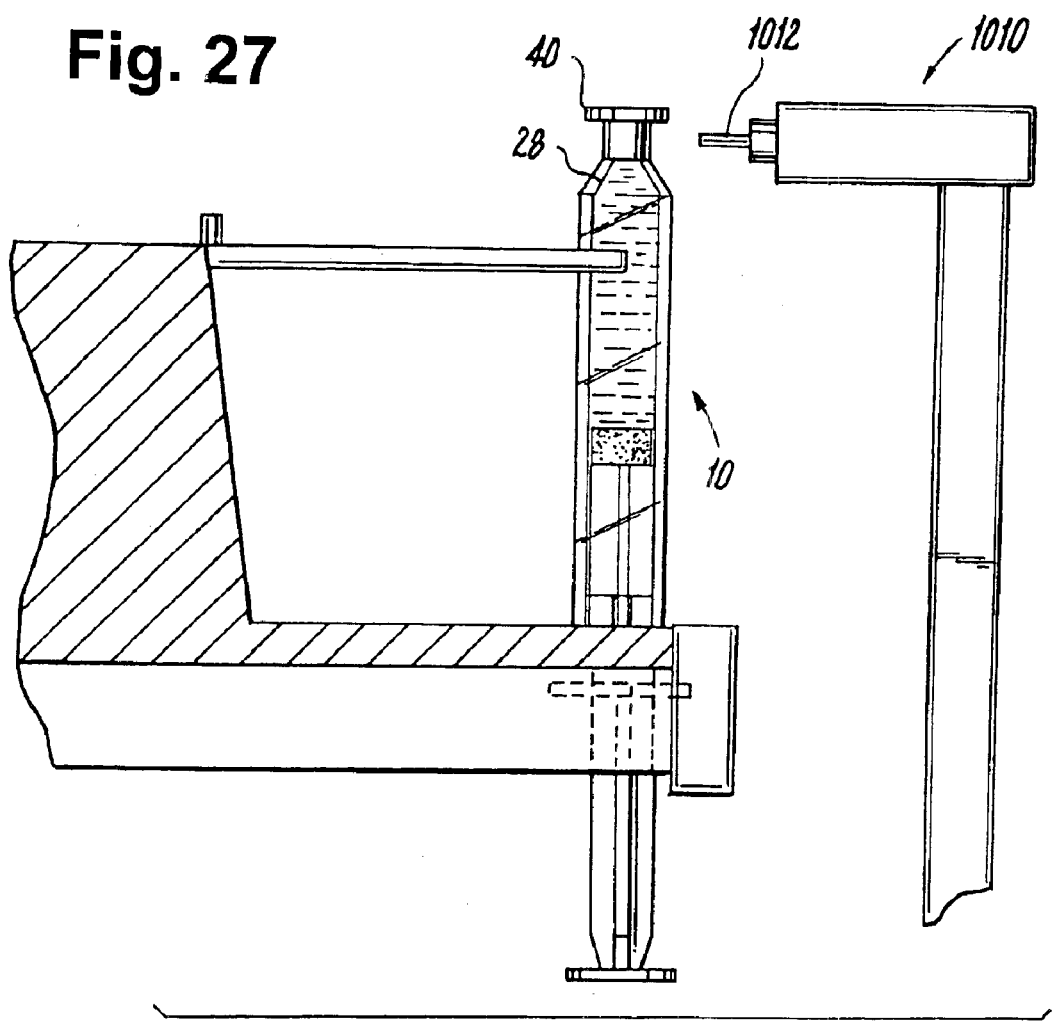
FIG. 27 is a side elevation of one exemplary device for providing a tamper evident syringe.

In yet another embodiment and as illustrated in FIGS. 27 and 28, station 197 is a station where an ultrasonic welding operation is performed by an ultrasonic welder 1010 or the like. Ultrasonic welding is a process used to join plastic parts through pressure and high frequency mechanical vibrations, creating localized frictional heat that melts the plastic together. When the vibrations stop, the plastic quickly cools and solidifies resulting in a localized spot weld between the two plastic parts, which in the present case is namely the tip cap 40 and the underlying syringe part, e.g., barrel tip luer connection 28. As is illustrated, the tip cap 40 has a flange that extends down from a top cover portion and this annular flange is the portion that extends around (circumscribes) the barrel tip luer connection 28 when the tip cap 40 is properly secured to the barrel tip luer connection 28 as by threads, snap-fit, etc. Accordingly, the spot weld is typically located at some location along the flange of the tip cap 40. As mentioned, the ultrasonic welder 1010 typically has a tool 1012 or the like which is placed into contact with or in close proximity to an outer surface of the flange of the tip cap 40 and then a horn of the welder 1010 acts as an acoustic tool and transfers vibratory energy directly to the parts being assembled (tip cap 40 and the syringe barrel) and it also applies a welding pressure. The vibrations are transmitted through the workpiece to the joint area. Here the vibratory energy is converted to heat through friction—this then softens or melts the plastic and joins the plastic parts together. It will be appreciated that the welding operation can be repeated and more than one localized weld spot can be created around the periphery of the tip cap 40.

Since ultrasonic welding is very fast (weld times are typically less than 1 second) and easily automated, it is particularly suited for use in the present system 100 for the purpose of creating a tamper proof tip cap 40. As with the heat-staking operation, the ultrasonic welding operation produces a small area of bonding between the tip cap 40 and the syringe barrel 28 such that when the user twists the tip cap 40, the user should feel noticeable resistance and hear a "snap" noise that evidences that the two plastic parts are bonded together and have not been tampered with since the bonding operation was performed.

In yet another embodiment illustrated in FIGS. 31–37, the tamper evident processing station can include an automated tip taper device which is configured to place tamper evident tape over the end of the syringe. In other words, the automated device disposes and affixes one end of the tamper evident tape to an outer surface of the syringe barrel and then wraps the tape over and on top of the tip cap 40 before affixing the other end of the tape to the other side of the syringe barrel. The tape should be tightly fit across the tip cap so that it is under an amount of tension when it is placed on and over the tip cap so that any type of twisting or removal or attempted removal of the tip cap will result in the tape being damaged in some way. In other words, by viewing the appearance and integrity of the tamper evident tape, the user can tell if the syringe 10 has been or may have been tampered with and therefore should not be used but rather should be discarded.

Figure 37:
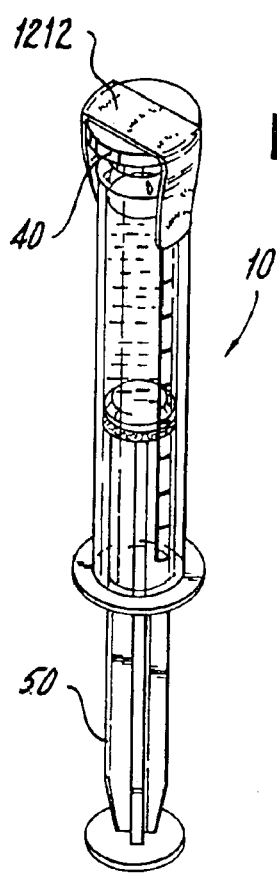
FIG. 37 is a view of a syringe with tamper evident tape attached thereto about the tip cap.

FIGS. 31–34 illustrate one device that is capable of producing a tamper evident syringe. More specifically, a tamper evident tape sealing station 1200 is provided for applying a section of tape over the tip cap of the syringe, with the ends of the tape being affixed to the syringe barrel as shown in FIG. 37. The station 1200 includes an assembly 1210 for applying a tamper tape 1212 about the tip cap 40 of the syringe 10. The assembly 1210 has a base 1214 with a standoff 1216 extending upwardly therefrom. Formed along a length of the standoff 1216 are a collar 1218, a moveable syringe slide 1220, and a cutting mechanism 1222 for selectively cutting the tape. The tape 1212 is initially provided in a roll form with the tape 1212 being wound about a core 1224 that is mounted on a cylinder mount 1226. The tape 1212 is fed from the roll to a tape guide mechanism 1230. The tape guide mechanism 1230 includes a roller 1232 and tape guide 1234 that receives the tape 1212 from the roller 1232 and feeds into down to an applicator device. A tape guide rod 1236 is provided and runs the length of the tape guide 1234. A tape wipe plate 1240 includes a first roller 1242 and a second roller 1244 along with a cap roller 1246. The tape 1212 is fed down the tape guide 1234 in an indexed fashion to one of the rollers 1242, 1244 which applies pressure to the tape 1212 and presses the tape into contact with one side of the syringe barrel so as to securely attach the tape thereto and then by action of the applicator mechanism, the tape is then applied across the top of the tip cap 40 by means of the cap roller 1246 which attaches the tape thereacross and then the roller applies the tape to the other side of the barrel.

Figure 33:
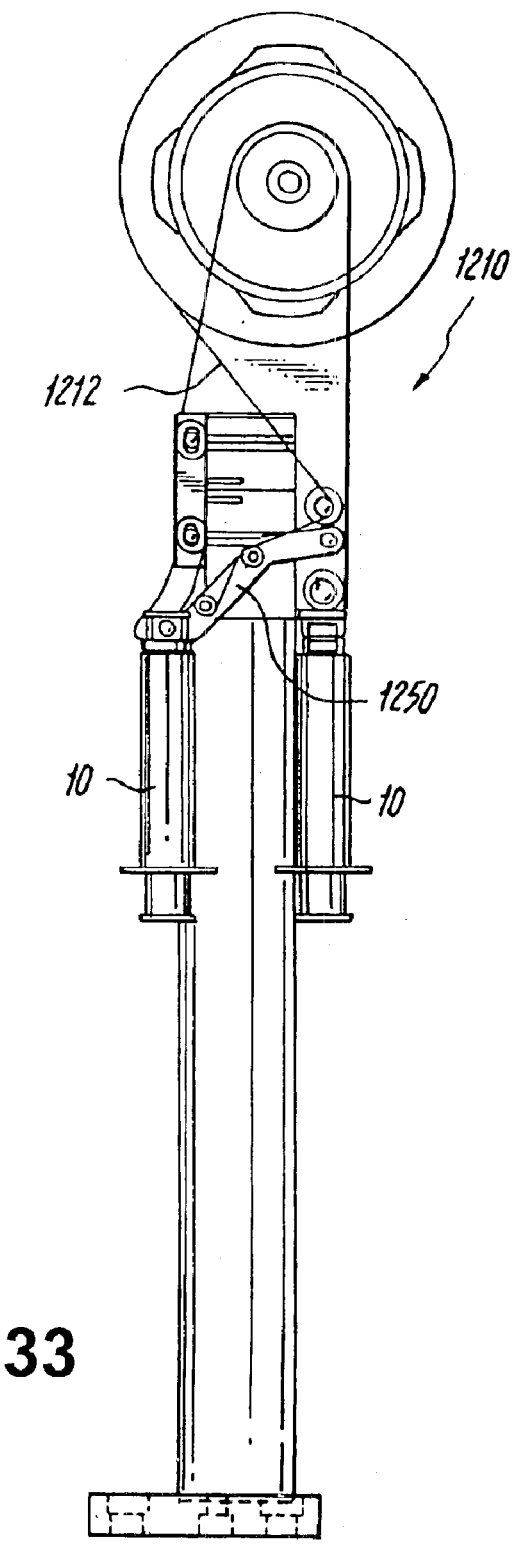
FIG. 33 is a side elevation view of the tape sealing device in a first operating position.
Figure 34:
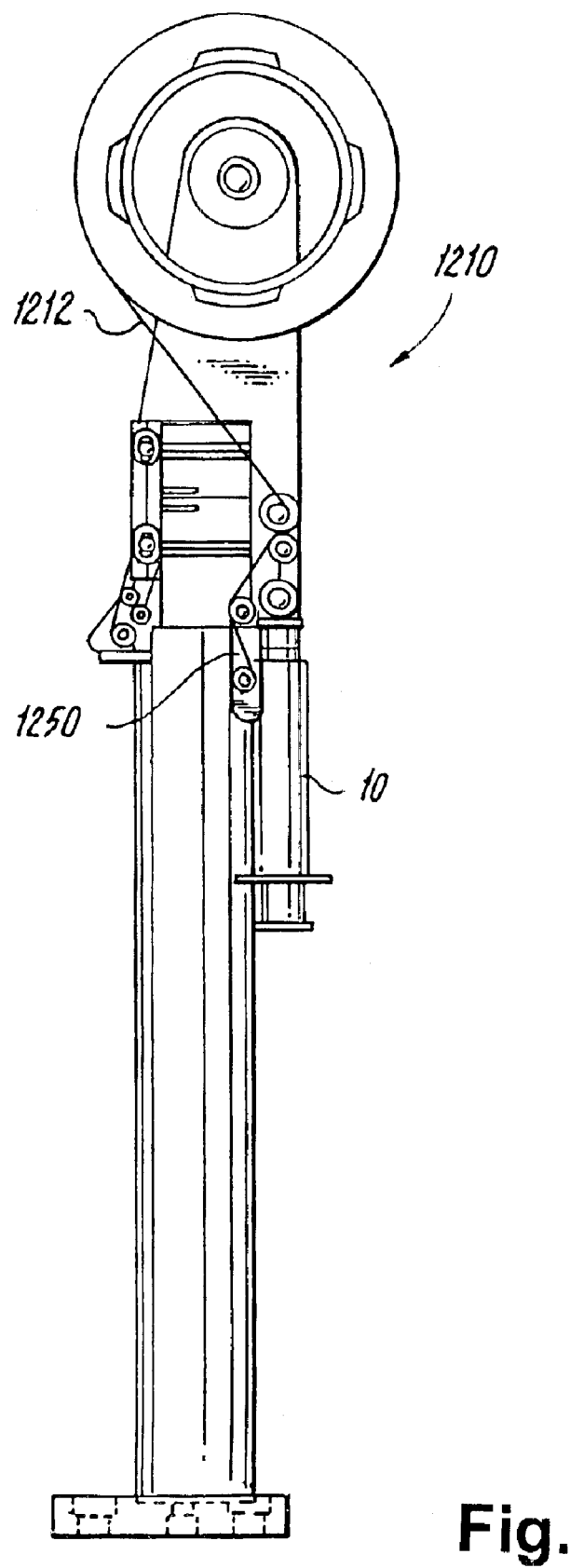
FIG. 34 is a side elevation view of the tape sealing device in a second operating position.

The syringes 10 are received from the rotary device 130 and the syringe slide 1220 serves to apply pressure to the syringes that are held in the pockets of the rotary device 130 so that the syringes do not move during the application of the tape. After the tape is applied to one cap, an index arm 1250 will go to idle position and the tape is cut at next start and the index arm will come down and start taping the next syringe (FIGS. 33–34). If there is no syringe, the dial finger (part of dial 130) will index the tape arm to the first syringe and start taping on barrel. The tape will make contact in idle index mode.

Figure 35:
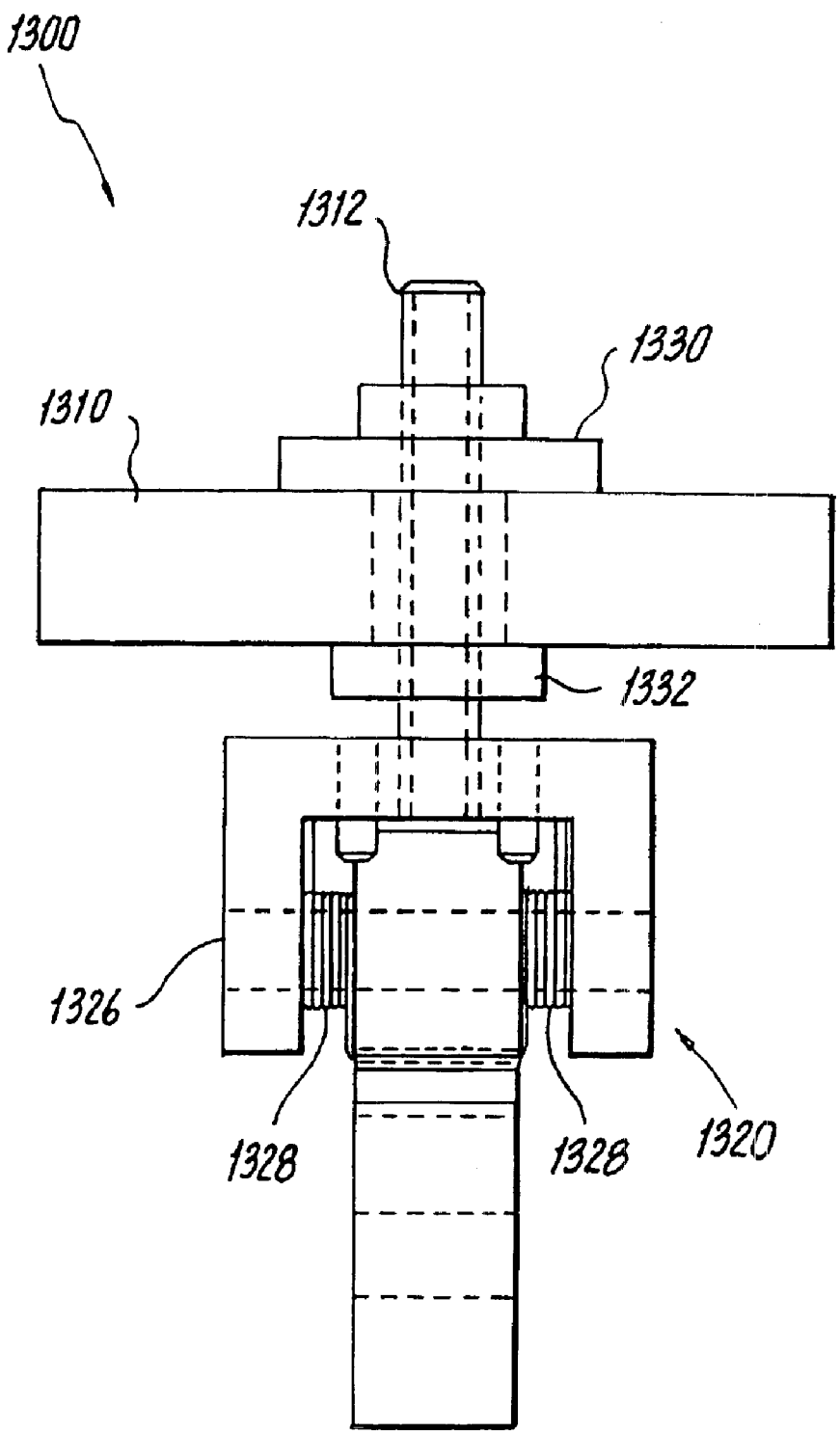
FIG. 35 is a top plan view of a secondary tamper tape wiper.
Figure 36:
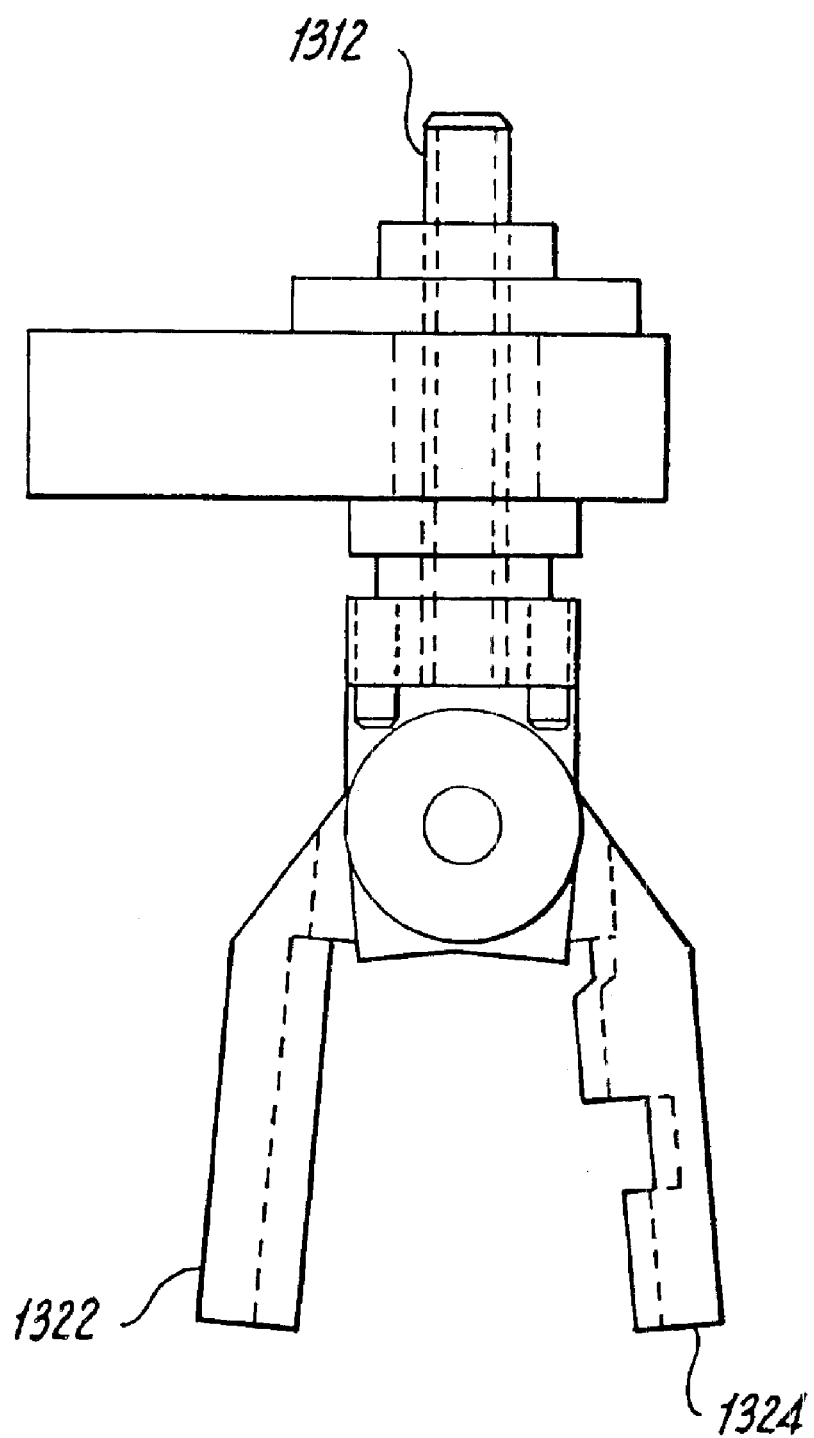
FIG. 36 is a side elevation view of the wiper of FIG. 35 in an open condition.

FIGS. 35–36 illustrate in close up a tamper tape secondary wipe assembly 1300. The assembly 1300 includes an output cutter top plate 1310 that has an opening formed therethrough for receiving a shaft 1312 that is coupled to a bandolier wipe clevis 1320 that is generally a U-shaped member. A bandolier front wipe 1322 and bandolier rear wipe 1324 are held between the bandolier wipe clevis 1320 in a pivotable manner. More specifically, first ends of the wipes 1322, 1324 are pivotably coupled to the clevis 1320 by a pin 1326 with springs 1328 being disposed between each side face of the wipes 1322, 1324 and the facing wall of the clevis 1320. A bandolier wipe top stop 1330 and bandolier wipe stop 1332 are also provided. The wipe assembly 1300 is designed to apply pressure to the tape to ensure that the tape is securely fixed to the bandoliered syringe.

Figure 38:
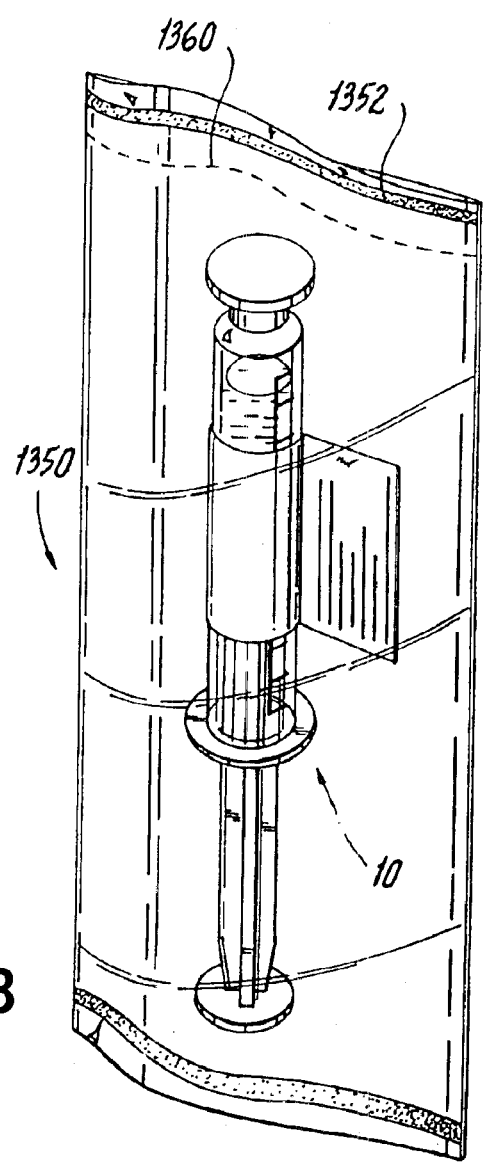
FIG. 38 is a view of a syringe disposed into a sealed plastic bag.

FIG. 38 illustrates another means for providing a tamper evident syringe. More specifically, the prepared syringe 10 is disposed within a plastic body 1350 and then sealed (e.g., as by heat) to provide another tamper proof evident solution. In other words, the syringe lies between two sheets of plastic material and a first seal (e.g., heat seal) 1352 is formed across the sheets and then a second seal 1354 is formed across the plastic material with the syringe 10 disposed between the seals 1352, 1354. The body 1350 is otherwise joined along its sides so that the result of the sealing action is that a sealed bag 1350 is formed. A perforated line 1360 is formed in the bag 1350 near one of the seals 1352, 1354 to permit the bag to be opened. The plastic bag 1350 is formed such that it is free of electrostatic charges.

The user can easily see if the syringe 10 has been tampered with by simply observing the condition of the bag 1350. If the bag 1350 is not in a completely sealed condition, the user should not use the syringe 10 as it should be treated as being tampered with. It will further be appreciated that conventional shrink wrapping techniques can be used as a means for providing a tamper evident proof solution for the distribution of syringes.

It will be appreciated by persons skilled in the art that the present invention is not limited to the embodiments described thus far with reference to the accompanying drawings; rather the present invention is limited only by the following claims.

What is claimed is:

1. An automated medication preparation system including automated syringe preparation comprising:
   a first automated gripping means for removing a tip cap from a barrel of one syringe and placing the removed tip cap at a first location;
   an automated device for delivering a prescribed dosage amount of medication to the syringe by injecting the medication through the uncapped barrel in a just-in-time for use manner;
   a second automated gripping means for replacing the removed tip cap on the syringe barrel after the medication is injected therein; and
   a coupling device for joining the tip cap to the syringe barrel in a local area to produce a tamper evident syringe, wherein the syringe is automatically advanced from the second automated gripping means to the coupling device.

2. The automated system of claim 1, wherein each of the first and second automated gripping means comprises a robotic device having first and second gripping arms that are spaced apart from one another in a first position and are moved toward one another to a second position so as to securely capture and hold the tip cap between the first and second gripping arms.

3. The automated system of claim 2, wherein the robotic device is movable at least along an x axis and a y axis.

4. The automated system of claim 1, further including:
   a post at the first location for receiving and holding the removed tip cap.

5. The automated system of claim 1, further including:
   an automated device for extending a plunger of the syringe barrel.

6. The automated system of claim 5, wherein the automated device is operatively connected to a control unit which instructs the automated device to extend the plunger a predetermined distance based on the prescribed amount of medication.

7. The automated system of claim 1, further including an automated rotary device that is indexed to advance the syringe from one station to another station, the rotary device having a first feature formed as part thereof for releasably retaining the syringe and a second feature for holding the removed tip cap as the syringe is advanced from one station to the next.

8. The automated system of claim 1, wherein the automated device for delivering a prescribed dosage amount of medication to the syringe comprises a robotic device having a pivotable arm that includes a platform section having a first face and an opposing second face, a cannula extending through the platform away from the first face for receiving the medication from a supply, the cannula being operatively connected to an apparatus that draws the medication from the supply into the cannula when actuated.

9. The automated system of claim 8, wherein the apparatus comprises an aspirating device that applies negative pressure to an interior of the cannula to cause the medication to be drawn from the supply to the cannula.

10. The automated system of claim 1, wherein the first and second gripping means, the automated delivery device and the coupling device are all part of an indexed system in which the syringe is automatically advanced from one station to a next station.

11. The automated system of claim 1, wherein the coupling device comprises a heat-staking device including a tool for transferring heat to the tip cap resulting in localized melting of the tip cap and bonding to an outer surface of a syringe luer connector.

12. The automated system of claim 11, wherein the tool is selected from the group consisting of a heated wire and a heated probe.

13. The automated system of claim 1, wherein the tip cap is joined to a syringe luer connector at a plurality of locations circumferentially around the tip cap.

14. The automated system of claim 1, wherein the coupling device comprises a laser that emits a laser beam that causes the joining between the tip cap and a syringe luer connector in the local area.

15. The automated system of claim 1, wherein the coupling device comprises an ultrasonic welder that joins the tip cap and the syringe barrel through pressure and high frequency mechanical vibrations, creating localized frictional heat that melts the tip cap and syringe luer connector together, both of which are formed of a plastic material.

16. The automated system of claim 1, wherein the coupling device is in communication with a controller that controls a temperature of a direct contact-heated tool and monitors and controls a time period that the tool is in contact with the tip cap.

17. The automated system of claim 1, wherein the tip cap and a syringe luer connector are joined at a spot weld that has a substantially circular shape.

18. The automated system of claim 1, wherein the coupling device comprises a heat-stake device that includes a plurality of interchangeable direct contact-heated tools.

19. The automated system of claim 1, further including:
an automated member for receiving and holding the syringe barrel after it is has been filled so that the movement thereof is prevented when the coupling device acts on the syringe to join the tip cap to the syringe barrel.

20. The automated system of claim 1, wherein the coupling device is a tamper evident tape dispenser that disperses tape and presses the tape into contact with one side of the syringe barrel and then directing the tape up the syringe barrel to the tip cap where the tape is laid across a top of the tip cap and then down an opposite side of the syringe barrel.

21. An automated medication preparation system including automated syringe preparation comprising:
a first automated device for removing a tip cap from a barrel of one syringe and placing the removed tip cap at a first location;
an automated transfer device for delivering a prescribed dosage amount of medication to the syringe by injecting the medication through the uncapped barrel in a just-in-time for use manner;
a second automated device for replacing the removed tip cap on the syringe barrel after the medication is injected therein; and
a station for making the syringe tamper evident, the station including a device for joining the tip cap to the syringe barrel in a local area by heating and reflowing a section of the tip cap into contact with the syringe barrel whereupon cooling, a local weld is formed between the tip cap and the syringe barrel, wherein the syringe is automatically advanced from the second automated device to the station for making the syringe tamper evident.

22. The system of claim 21, wherein the weld is formed between a flange of the tip cap and an outer hub of the syringe barrel.

23. The automated system of claim 21, wherein the device for joining the tip cap to the syringe luer connector comprises a heat-staking device including a tool for transferring heat to the tip cap resulting in localized melting of the tip cap and bonding to an outer surface of the syringe barrel.

24. The automated system of claim 23, wherein the tool is selected from the group consisting of a heated wire and a heated probe.

25. The automated system of claim 23, wherein the tip cap is joined to the syringe luer connector at a plurality of locations circumferentially around the tip cap and wiping a tamper evident tape around the tip cap.

26. The automated system of claim 21, wherein the device for joining the tip cap to the syringe luer connector comprises a laser that emits a laser beam that causes the joining between the tip cap and the syringe barrel in the local area.

27. The automated system of claim 21, wherein the device for joining the tip cap to the syringe luer connector comprises an ultrasonic welder that joins the tip cap and the syringe luer connector through pressure and high frequency mechanical vibrations, creating localized frictional heat that melts the tip cap and syringe luer connector together, both of which are formed of a plastic material.

28. The automated system of claim 21, wherein the device for joining the tip cap to the syringe luer connector is in communication with a controller that controls a temperature of a direct contact-heated tool and monitors and controls a time period that the tool is in contact with the tip cap.

29. An automated medication preparation system including automated syringe preparation comprising:
a first automated gripping means for removing a tip cap from a barrel of one syringe and placing the removed tip cap at a first location;
an automated device for delivering a prescribed dosage amount of medication to the syringe by injecting the medication through the uncapped barrel in a just-in-time for use manner;
a second automated gripping means for replacing the removed tip cap on the syringe barrel after the medication is injected therein; and
a mechanism for capturing the syringe containing the prescribed dosage amount between two sheets of plastic material and then evacuating air from between the sheets to form and capture the syringe in a shrink wrapped package which has a perforated seam formed therein to assist a user in opening of the package.

30. An automated medication preparation system including automated syringe preparation comprising:
a plurality of stations for removing a tip cap from a barrel of one syringe, delivering a prescribed dosage amount of medication to the syringe in a just-in-time for use manner, and replacing the removed tip cap on the syringe luer connector after the medication is delivered thereto; and
a station for making the syringe tamper evident, the station including a device for joining the tip cap to a syringe luer connector in a local area by forming a local weld between the tip cap and the syringe luer connector so as to restrict twisting and removal of the tip cap, wherein the syringe is automatically advanced from the second automated device to the station for making the syringe tamper evident.

31. A method for just-in-time removal of a tip cap from a syringe barrel, filling the syringe with a prescribed dose of medication, replacing the tip cap on the syringe barrel and making the syringe tamper evident, the method including the steps of:
removing the tip cap from the syringe luer connector to open the syringe barrel and placing the removed tip cap at a first location;
delivering the prescribed dose to an interior of the syringe barrel;
gripping the removed tip cap at the first location and moving it to the syringe barrel containing the prescribed dose;
replacing the tip cap on a syringe luer connector; and
joining the tip cap to the syringe luer connector in a local area by heating and reflowing a section of the tip cap into contact with the syringe luer connector whereupon cooling, a local weld is formed between the tip cap and the syringe luer connector, wherein the syringe is automatically advanced from a station where the tip cap is replaced to a station for making the syringe tamper evident where the local weld is formed.

32. The method of claim 31, wherein the step of delivering the prescribed dose comprises the steps of:

providing a robotic fluid transfer device having a cannula unit that is positioned between first and second positions, wherein the cannula unit includes a cannula;

connecting the cannula to an apparatus that draws the prescribed dose from a medication supply to the cannula when the apparatus is actuated and the cannula unit is in the first position;

moving the robotic fluid transfer device to the second position; and delivering the prescribed dose into the syringe body through an entrance port created when the tip cap is removed.

33. The method of claim 32, wherein the apparatus aspirates the prescribed dose from the medication supply.

34. The method of claim 32, further including the steps of:

providing an automated device for extending a plunger of the syringe; and extending the plunger a predetermined distance based upon a volume of the prescribed dose.

35. The method of claim 31, wherein the step of joining the tip cap to the syringe barrel comprises the steps of:

providing a heat-stake device that includes a direct contact-heated tool;

heating the tool to a predetermined temperature and placing the tool into contact with an outer surface of the tip cap;

directing the tool into the tip cap by applying a predetermined pressure thereto causing a local section of the tip cap to melt and reflow into contact with an outer surface of the syringe luer connector; and removing the tool such that the reflow cools and the local weld is formed.

36. The method of claim 31, wherein the step of joining the tip cap to the syringe luer connector comprises the steps of:

providing an ultrasonic welder that includes a probe;

activating the welder so as to create vibratory energy that is transferred through the probe directly to the tip cap and the syringe luer connector, while the probe simultaneously applies a welding pressure; and transmitting the vibrations through the tip cap and syringe luer connector to a joint area where the vibratory energy is converted to heat through friction which causes the tip cap and the syringe luer connector to melt, whereby the tip cap is joined to the syringe barrel.

37. The method of claim 31, wherein the step of joining the tip cap to the syringe barrel comprises the steps of:

providing a laser;

directing an emitted laser beam to an outer surface of the tip cap to cause a local section of the tip cap to melt and reflow into contact with an outer surface of the syringe luer connector; and deactivating the laser such that the reflow cools and the local weld is formed.

38. The method of claim 31, further including the step of:

receiving and holding the syringe barrel with a gripper member after the tip cap has been replaced but prior to the joining the tip cap to the syringe barrel.

* * * * *